US008013217B2

(12) United States Patent
Wu et al.

(10) Patent No.: US 8,013,217 B2
(45) Date of Patent: Sep. 6, 2011

(54) HIGH YIELDING SOYBEAN PLANTS WITH LOW LINOLENIC ACID

(75) Inventors: Kunsheng Wu, Ballwin, MO (US); Paul McLaird, Kirkwood, MO (US); Joseph Byrum, West Des Moines, IA (US); Robert Reiter, Baldwin, MO (US); Mark Erickson, Slater, IA (US)

(73) Assignee: Monsanto Technology LLC, St. Louis, MO (US)

( * ) Notice: Subject to any disclaimer, the term of this patent is extended or adjusted under 35 U.S.C. 154(b) by 206 days.

(21) Appl. No.: 12/212,624

(22) Filed: Sep. 17, 2008

(65) Prior Publication Data

US 2009/0193547 A1 Jul. 30, 2009

Related U.S. Application Data

(62) Division of application No. 11/239,676, filed on Sep. 29, 2005, now Pat. No. 7,442,850.

(60) Provisional application No. 60/614,331, filed on Sep. 29, 2004.

(51) Int. Cl.
*A01H 5/00* (2006.01)
(52) U.S. Cl. ........................................ 800/298; 800/267
(58) Field of Classification Search ........................ None
See application file for complete search history.

(56) References Cited

U.S. PATENT DOCUMENTS

| | | | | |
|---|---|---|---|---|
| 5,530,183 | A | 6/1996 | Fehr et al. | 800/200 |
| 5,534,425 | A | 7/1996 | Fehr et al. | 435/172.1 |
| 5,710,365 | A | 1/1998 | Kerr et al. | 800/200 |
| 5,710,369 | A | 1/1998 | Fehr et al. | 800/200 |
| 5,714,668 | A | 2/1998 | Fehr et al. | 800/200 |
| 5,714,669 | A | 2/1998 | Fehr et al. | 800/200 |
| 5,714,670 | A | 2/1998 | Fehr et al. | 800/200 |
| 5,763,745 | A | 6/1998 | Fehr et al. | 800/200 |
| 5,850,030 | A | 12/1998 | Fehr et al. | 800/312 |
| 5,986,118 | A | 11/1999 | Fehr et al. | 554/224 |
| 6,133,509 | A | 10/2000 | Fehr et al. | 800/312 |
| 6,184,442 | B1 | 2/2001 | Nickell | 800/312 |
| 6,369,302 | B1 | 4/2002 | Matson | 800/312 |
| 2004/0107460 | A1 | 6/2004 | Fillatti et al. | 800/281 |

FOREIGN PATENT DOCUMENTS

WO    WO 04/001000    12/2003

OTHER PUBLICATIONS

Voelker et al, Ann Rev Plant Physiol and Plant Mol Biol 52: 335-361, 2001.*
GenBank Accession No. AY204710, dated May 17, 2005.
GenBank Accession No. AY204712, dated May 17, 2005.
Fehr et al., "Breeding for modified fatty acid composition in soybean," *Crop Sci.*, 47(S3):S72-S87, 2007.
GenBank Accession No. AY204711, dated May 17, 2005.
Anai et al., "Identification of corresponding genes for three low-alpha-linolenic acid mutants and elucidation of their contribution to fatty acid biosynthesis in soybean seed," *Plant Science* 168:1615-1623, 2005.
Bilyeu et al., "Molecular genetics of low linolenic acid soybeans," *10th Biennial Conference Of The Cellular And Moecular Biology Of The Soybean*, 2004.
Bilyeu et al., "The contribution of multiple genes to one trait: Linolenic acid production in soybean seeds," *Plant Genetics 2003: Mechanisms of Genetic Variation, American Society of Plant Biologists*, Abstract 50, XP009060561, 2003.
Bilyeu et al., "Three microsomal omega-3 fatty-acid desaturase genes contribute to soybean linolenic acid levels," *Crop Sci*, 43(5):1833-1838, 2003.
Byrum, et al., "Alteration of the omega-3 fatty acid desaturase gene is associated with reduced linolenic acid in the A5 soybean genotype," *Theor. Appl. Genet.*, 94:356-359, 1997.
Fehr et al., "Inheritance of reduced linolenic acid content in soybean genotypes a16 and a17," *Crop Sci.*, 32:903-906, 1992.
Jourdren et al., "Specific molecular marker of the genes controlling linolenic acid content in rapeseed," *Theor Appl Genet*, 93:512-518, 1996.
Knutzon et al., "Modification of Brassica ssed oil by antisense expression of a stearoyl-cyl carrier protein desaturase gene," *Proc. Natl. Acad. Sci. USA*, 89:2624-2628, 1992.
Lui et al., "Oxidative stability of soybean oils with altered fatty acid composition," *J. Am. Oil Chem. Soc.*, 69:528-532, 1992.
O'Brien, "Fats and oils: formulating and processing for applications," Second Edition, CRC Press, 14-15, 2003.
Primomo et al., "Inheritance and interaction of low palmitic and low linolenic soybean," *Crop Sci.*, 42:31-36, 2002.
Rahman et al., "Inheritance of reduced linolenic acid content in soybean seed oil," *Theor. Appl. Genet.*, 94:299-302, 1997.
Rahman et al., "Genetic relationships of soybean mutants for different linolenic acid contents," *Crop Sci.*, 38:702-706, 1998.
Rennie et al., "New allele at the fan locus in the soybean line A5," *Crop Sci*, 31:297-301, 1991.
Ross et al., "Agronomic and seed traints of 1%-linolenate soybean genotypes," *Crop Sci.*, 40:383-386, 2000. Stoisin et al., "Inheritance of low linolenic acid level in the soybean line RG10," *Crop Sci.*, 38:1441-1444, 1998.
Walker et al., "Reduced-linolenate content associations with agronomic and seed traits of soybean," *Crop Sci*, 38:352-255, 1998.
Wilcox et al., "Gene symbol assigned for linolenic acid mutant in the soybean," *J. Heredity*, 78:410, 1987.
Wilcox et al., "Inheritance of low linolenic acid content of the seed of a mutant of *Glycine max*," *Theor. Appl. Genet.*, 71:74-78, 1985.
Yadev et al., "Cloning of higher plant ω-3 fatty acid desaturases," *Plant Physiol.*, 103:467-476, 1993.
Bilyeu et al., "Molecular genetic resources for development of 1% linolenic acid soybeans," *Crop Sci.*, 46:1913-1918, 2006.
Bilyeu et al., "Novel FAD3 mutant allele combinations produce soybeans containing 1% linolenic acid in the seed oil," *Crop Sci.*, 51(1):259-264, 2011.
Reinprecht et al., "Molecular basis of the low linolenic acid trait in soybean EMS mutant line RG10," *Plant Breeding*, 128:253-258, 2009.

* cited by examiner

*Primary Examiner* — Elizabeth McElwain
(74) *Attorney, Agent, or Firm* — Chunping Li, Esq.; SNR Denton US LLP

(57) ABSTRACT

The invention overcomes the deficiencies of the prior art by providing methods for marker assisted selection to create plants of a soybean variety that exhibit a mid/low linolenic acid content with a commercially significant yield and an agronomically elite phenotype. The invention also provides derivatives and plant parts of these plants. Further provided by the invention are methods for the use of these plants. The invention is significant in that oil with decreased linolenic acid exhibits numerous beneficial characteristics yet prior art varieties with decreased linolenic acid also exhibited decreased yield and poor agronomic quality.

19 Claims, 2 Drawing Sheets

SEQUENCE LISTING

<160> NUMBER OF SEQ ID NOS: 98

<210> SEQ ID NO 1
<211> LENGTH: 2683
<212> TYPE: DNA
<213> ORGANISM: Glycine max

<400> SEQUENCE: 1

```
gttcaagcac agcctctaca acatgttggt aatggtgcag ggaaagaaga tcaagcttat    60
tttgatccaa gtgctccacc acccttcaag attgcaaata tcagagcagc aattccaaaa   120
cattgctggg agaagaacac attgagatct ctgagttatg ttctgaggga tgtgttggta   180
gtgactgcat yggtagctgc agcaatcggc ttcaatagct ggttcttctg gccactctat   240
yggcctgcac aaggcacaat gttttgggca cttttttgttc ttggacatga ttggtaacta   300
attattatta caaattgtta tgttatgtta tgttatgttg ttgtgccttt ttctcagtga   360
tgctttagtc atttcatttc acttggttat gcatgattgt tcgttcatat gttctgtcat   420
ggtgagttct aatttgattg atgcatgaa cagtggtcat ggaagttttt caaacagtcc    480
tttgttgaac agcattgtgg gccacatctt gcactcttca attcttgtac cataccatgg   540
atggtcggtt cctttagca acttttcatg ttcactttgt ccttaaattt tttttatgt    600
ttgttaaaaa atctttggtc tgatttaaca acctaaccat tttacaacw catggatttw   660
ttgcaggaga attagccaca ggactcacca tcagaaccat ggccatgttg agaaggatga   720
atcatgggtt ccggtattac tatgagtttg cttgattaat ttccacattt tttctttctt   780
cttaattttta atcagtggtt agatttggtt gtgttccaat agaagaaaag ggggtatcta   840
gagagatgtg aatttcatga agtggttcat gattatgtgt ctttatgcct ttatgtcagc   900
ttacagagaa agtttacaag aatctagaca acatgacaag aatgatgaga ttcactcttc   960
cttcccccat ctttgcatac ccctttttatt tggtgagacc ctcttttttcc agaatgacag  1020
cattattttta ctatatagta cctcaatttt tatattctta aaattttgaa ttcttgaaat  1080
tgaaaggaaa ggacttttatt gggtctagca tctcactctc tctttgtgat atgaaccata  1140
tatttcagtg gagcagaagc cctggaaaag aaggctctca tttcaaccct tacagcaact  1200
tgttctctcc tggtgagaga agagatgtgc taacttcaac tctgtgttgg ggcatcatgc  1260
tttctgtgct tctctatctt tccctcacaa tgggtccact ttttatgctc aagctctatg  1320
gggttcccta tttggtaatc tcactctcac actttcttta tacatcgcac accagtgtgg  1380
gttatttgca acctacaccg aagtaatgcc ctataattaa tgaggttaac acatgtccaa  1440
gtccaatatt tgttcactt atttgaactt gaacatgtgt agatcttcgt catgtggctg  1500
gatttcgtca cgtacttgca tcatcatggt tacaagcaga aactgccttg gtaccgtggc  1560
caggtatccc atttaacaca atttgtttca ttaacatttt aagagaattt ttttttcaaa  1620
atagtttcg aaattaagca ataccaagc aaattgttag atctacgctt gtacttgttt  1680
taaagtcaaa ttcatgacca aattgtcctc acaagtccaa accgtccact attttatttt  1740
cacctacttt atagcccaat ttgtcatttg gttacttcag aaaagagaac cccatttgta  1800
gtaaatatat tatttatgaa ttatggtagt ttcaacataa aacatattta tgtgcagttt  1860
tgccatcctt caaaagaaga tagaaactta ctccatgtta ctctgtctat atgtaatttc  1920
acaggaatgg agttatctaa ggggtggtct tacaacagta gatcgcgact atggttggat  1980
caacaacatt caccatgaca ttggcaccca tgttatccat cacctttttcc ctcaaattcc  2040
acattatcat ttaatcgaag cggtattaat tctctatttc acaagaaatt attgtatgtc  2100
tgcctatgtg atctaagtca atttttcacat aacacatgat caaactttct taattctttc  2160
ttctaaattg aaaagtgga ttatatgtca attgaaaatt ggtcaagacc acaaacatgt  2220
gatgatctcc cacctacat ataataattt ctcctattct acaatcaata atccttctat  2280
ggtcctgaat tgttcctttc ttttttcatt ttcttattct ttttgttgtc ccacaataga  2340
```

```
ctaaagcagc aaaggcagtg ctaggaaagt attatcgtga gcctcagaaa tctgggccat    2400
tgccacttca tctaataaag tacttgctcc acagcataag tcaggatcac ttcgttagcg    2460
actctggcga cattgtgtac taccagactg attcccagct ccacaaagat tcttggaccc    2520
agtccaacta aagttttga tgctacattt acctatttca ctcttaaata ctatttccta    2580
tgtaatatgt aatttagaat atgttaccta ctcaaatcaa ttaggtgaca tgtataagct    2640
ttcataaatt atgctagaaa tgcacttact ttacaaagca tgc                     2683

<210> SEQ ID NO 2
<211> LENGTH: 4160
<212> TYPE: DNA
<213> ORGANISM: Glycine max

<400> SEQUENCE: 2
aaagatttca ttcttcctct tctaggttat tacgcaccac ccaccacgta tccctgaaag      60
agagaaaaac acactaagcc aaagccaaag cagcaatggt taaagacaca aagcctttag     120
cctatgctgc taataatgga taccaaaagg aagcttttga tcccagtgct cctccaccgt     180
ttaagattgc agaaatcaga gttgcaatac caaaacattg ctgggtcaag aatccatgga     240
gatccctcag ttatgttctc agggatgtgc ttgtaattgc tgcattgatg ctgctgcaa      300 gtcacttcaa caactggctt ctctggctaa tctattggcc cattcaagga caatgttct      360 gggctctgtt tgttcttgga catgattggt aattaattat tgttgttac ttttttgtta     420 taatatgaat ctcacacact gctttgttat gcctacctca tttcatttgg ctttagacaa    480
cttaaatttg agatctttat tatgtttttt gcttatatgg taaagtgatt cattcttcac    540
attgaattga acagtggcca tggaagcttt tcagacagcc cttttctaaa tagcctggtg    600
ggacacatct tgcattcctc aattcttgtg ccataccatg gatggttagt tcatcccggc    660 tttttttgttt gtcattggaa gttctttat tgattcaatt tttatagcgt gttcggaaac     720
gcgtttcaga aaataatgaa atacatcttg aatctgaaag ttataacttt tagcttcatt    780
gtcattgaaa gttcttttat taattatatt tttattgcgt gtttggaatc ccatttgaga    840
aataagaaat cacgtttaaa atgtgaaagt tataactatt aactttttgac taaacttgaa    900 aaaatcacat ttttgatgtg gaaccaaatc tgatttgaga accaagttga ttttgatgga    960
ttttgcagga gaattagcca cagaactcac catcaaaatc atggacacat tgagaaggat   1020
gaatcctggg ttccagtatg tgattaacta cttcctctat agttatttt gattcaatta    1080 aatttattta tttaataagt tcaagaaaaa aggaatcttt atacttcatg ataaagctgt    1140
tcttgaacat tttttttgt cattatctta gttaaccgag aagatttaca agaatctaga    1200
caacatgaca agacttgtta gattcactgt gccatttcca ttgtttgtgt atccaattta    1260
tttggkgagk gcttttttt ttttacttgg aagactacaa cacattatta ttattataat    1320
atggttcaaa tcaatgactt ttaatttctt tgtgatgtgc actccatttt cagttctcaa    1380
gaagccccgg aaaggaaggt tctcacttca atccctacag caatctgttc ccacccagtg    1440
agagaaaggg aatagcaata tcaacactgt gttgggttac catgttttct atgcttatct    1500
atctctcctt cataactagt ccagttctat tgctcaagct ctatggaatt ccatattggg    1560
taattaaatt actcttacat tacttttcc tctttttttt tatgggtctt aactagtatc    1620
acaaaaatat tggttaaaaa atttaaaaa atatttatt atgtaaatca taaagaaca     1680 taaaaaaat gatgaataac ataatttcg tctcttatta aaatatttt tattttaaat    1740 ttcttaatca atatatttaa aatctggtta acattttttg aatatttcaa ttctccaatt    1800
```

```
aaaaatttga atagtcacc attaattatg taattgtttg aacacgtgca gatatttgtt      1860
atgtggctgg actttgtcac atacttgcat caccatggtc atcatcagaa actgccttgg      1920
tatcgcggca aggtaacaaa aataaataga aaatagtgag tgaacactta aatgttagat      1980
actaccttct tcttcttctt ttttttttt ttgaggttaa tgctagataa tagctagaaa       2040
gagaaagaaa gacaaatata ggtaaaaata aataatataa cctgggaaga agaaaacata      2100 aaaaagaaa taatagagtc tacgtaatgt ttggatttt gagtgaaatg gtgttcacct        2160
accattactc aaagattctg ttgtctacgt agtgtttgga cttggagtg aaatggtgtt       2220 cacctaccat tactcagatt ctgttgtgtc ccttagttac tgtcttatat tcttagggta     2280
tattctttat tttacatcct tttcacatct tacttkaaaa gatttttaat tattcattga     2340
aatattaacg tgacagttaa attaaaataa taaaaaattc gttaaaactt caaataaata     2400
agagtgaaag gatcatcatt tttcttcttt cttttattgc gttattaatc atgcttctct     2460
tctttttttt cttcgctttc cacccatatc aaattcatgt gaagtatgag aaaatcacga     2520
ttcaatggaa agctacagga actttttttg ttttgttttt ataatcggaa ttaatttata     2580
ctccattttt tcacaataaa tgttacttag tgccttaaag ataatatttg aaaaattaaa     2640
aaaattatta atacactgta ctactatata atatttgaca tatatttaac atgattttct     2700
attgaaaatt tgtatttatt atttttaat caaaacccat aaggcattaa tttacaagac      2760
ccatttttca tttatagctt tacctgtgat catttatagc tttaagggac ttagatgtta     2820
caatcttaat tacaagtaaa tatttatgaa aaacatgtgt cttacccctt aaccttacct     2880
caacaaagaa agtgtgataa gtggcaacac acgtgttgct tttttggccc agcaataaca     2940 cgtgttttttg tggtgtacaa aaatggacag gaatggagtt atttaagagg tggtctcaca    3000
actgtggatc gtgactatgg ttggatcaat aacattcacc atgacattgg cacccatgtt     3060
attcaccatc tttccctca aattcctcat tatcacctcg ttgaagcggt atattttact      3120
attattactc acctaaaaag aatgcaatta gtacattgt tttatctctt ggaagttagt      3180
cattttcagt tgcatgattg taatgttctc tctattttta aaccatgttt tcacacctac     3240
ttcgtttaaa ataagaatgt ggatactatt ctaatttcta ttaacttctt ttaaaaaata     3300
atgtaaaact agtattaaaa aagaggaaat agattacact ctactaatac taatagtata     3360
aaaaaaatta cattgttatt ttatcacaaa taattatata taattaattt ttacaatcat     3420
tatcttaaaa gtcatgtatg atatacagtt tttacatgct ttggtactta ttgtaaagtt     3480
agtgatttat tcattattta tgttatataa ttggcataaa tatcatgtaa ccagctcact     3540
atactataat gggaacttgg tggtgaaagg ggtttacaac cctctttct aggtgtaggt      3600 gctttgatac ttctggtccc ttttatatc aatataaatt atattttgct gataaaaaaa     3660
acattattaa tatataatca ttaacttctt taaaaaccgt acctaaaact ttatattatt     3720 aaaagaaga ttgagatcag caaagaaaa aaaattaac agtcatttga attcactgca        3780
gacacaagca gcaaaatcag ttcttggaga gtattaccgt gagccagaaa gatctgcaca     3840
ttaccatttc atctaataaa gtatttaatt cagagtatga gacaagacca cttcgtaagt     3900
gacactggag atgtggttta ttatcagact gattctctgc accttcactc gcaccgagac     3960
tgagtttcaa tttttgggtt atttattgga ttctagctac tcaaattact ttttttttaa     4020
tgttacgttt ttggagtttt aacgtttttct gaacaacttg caaattacat gcatagagag    4080
acaggaattc atagtgggcc tcaatggaat atttatttga aattagtaag gtggtaatta     4140
ataaatattg aattgtcagt                                                 4160
```

<210> SEQ ID NO 3
<211> LENGTH: 994
<212> TYPE: DNA
<213> ORGANISM: Glycine max

<400> SEQUENCE: 3

```
tgctacgaag caatttgcat gctaggaagc aaagtaaaat tctcaaactg tataacttat        60
tttctcttgt tgtatataaa actagtcatt tttcattaaa aagcattgta taatagttta       120
atgggtcatt gaattattta taattaatgt cattctattt ttaatactcc ttttgtttga       180
taatgattat cgtttcatgt tattttctat acatatcaag acaaattaat aaatggataa       240
aaaagtatca attttataaa attaatatta ttattattaa tttatttata atttttttgtt      300
atcatttata ttataagtaa tatattattg gcaaaaataa ttttttgatca attatattta      360
cctgtcggtc gaactctaga ttatgctggg tatcttctcc aaatgaatcc aaagattaaa      420
ataaaataaa attataagta atataaataa aaaacaatta atactagatt aacaagacta      480
aaataataat tattttataa tttattttct tcaataattg tagaatacaa ggagtaatat      540
ttaatgttgt ttaattcttg tttcaataat tgagatgttt tgaacaaatt aaataattat      600
tgtaaataga ataacattaa ttacaataat aaaatcattt taacgatcca ttaaacttaa      660
atgataaaat tcaactaact aatttggagt aattaagaaa aatagttaat ttagacaaca      720
atattaaatt tttgctaaat tatatgtttt tctcaaaatt acctataaca ttaataagac      780
atacttttat ttttcaaaga tttctactta attaaccgcc acaaattcat cctcgctggt      840
ttgtcctaca ccgtatgttt tttgacgtca gctaggcaaa ccaacataaa taggaagcag      900
tagaagtaaa agtagaatgt ggtagtgtta ttattattta ctactgtttc accttggtgt      960
tatataaatg cactaccccca taattgaatt tttc                                  994
```

<210> SEQ ID NO 4
<211> LENGTH: 24
<212> TYPE: DNA
<213> ORGANISM: Artificial Sequence
<220> FEATURE:
<223> OTHER INFORMATION: Synthetic Primer

<400> SEQUENCE: 4
cctattctag gttttacgc acca         24

<210> SEQ ID NO 5
<211> LENGTH: 25
<212> TYPE: DNA
<213> ORGANISM: Artificial Sequence
<220> FEATURE:
<223> OTHER INFORMATION: Synthetic Primer

<400> SEQUENCE: 5
aagttgtcta aagccaaatg aagaa        25

<210> SEQ ID NO 6
<211> LENGTH: 26
<212> TYPE: DNA
<213> ORGANISM: Artificial Sequence
<220> FEATURE:
<223> OTHER INFORMATION: Synthetic Primer

<400> SEQUENCE: 6
ggacatgatt ggtaataatt tttgtg       26

```
<210> SEQ ID NO 7
<211> LENGTH: 24
<212> TYPE: DNA
<213> ORGANISM: Artificial Sequence
<220> FEATURE:
<223> OTHER INFORMATION: Synthetic Primer

<400> SEQUENCE: 7
aggaagcata aagattccct tttt                                           24

<210> SEQ ID NO 8
<211> LENGTH: 23
<212> TYPE: DNA
<213> ORGANISM: Artificial Sequence
<220> FEATURE:
<223> OTHER INFORMATION: Synthetic Primer

<400> SEQUENCE: 8
aaagggaatc tttatgcttc ctg                                            23

<210> SEQ ID NO 9
<211> LENGTH: 24
<212> TYPE: DNA
<213> ORGANISM: Artificial Sequence
<220> FEATURE:
<223> OTHER INFORMATION: Synthetic Primer

<400> SEQUENCE: 9
tctgcacatg atcaaacaat taca                                           24

<210> SEQ ID NO 10
<211> LENGTH: 24
<212> TYPE: DNA
<213> ORGANISM: Artificial Sequence
<220> FEATURE:
<223> OTHER INFORMATION: Synthetic Primer

<400> SEQUENCE: 10
atgtaattgt ttgatcatgt gcag                                           24

<210> SEQ ID NO 11
<211> LENGTH: 24
<212> TYPE: DNA
<213> ORGANISM: Artificial Sequence
<220> FEATURE:
<223> OTHER INFORMATION: Synthetic Primer

<400> SEQUENCE: 11
aaaataaaat cttgtgggtg caat                                           24

<210> SEQ ID NO 12
<211> LENGTH: 23
<212> TYPE: DNA
<213> ORGANISM: Artificial Sequence
<220> FEATURE:
<223> OTHER INFORMATION: Synthetic Primer

<400> SEQUENCE: 12
tggcggatct atgtaaatga gtg                                            23

<210> SEQ ID NO 13
<211> LENGTH: 21
<212> TYPE: DNA
<213> ORGANISM: Artificial Sequence
<220> FEATURE:
<223> OTHER INFORMATION: Synthetic Primer

<400> SEQUENCE: 13
```
aatgaaaaac ggggcttgta a                                               21

<210> SEQ ID NO 14
<211> LENGTH: 24
<212> TYPE: DNA
<213> ORGANISM: Artificial Sequence
<220> FEATURE:
<223> OTHER INFORMATION: Synthetic Primer

<400> SEQUENCE: 14
ttttgttggt caagggactt agat                                            24

<210> SEQ ID NO 15
<211> LENGTH: 24
<212> TYPE: DNA
<213> ORGANISM: Artificial Sequence
<220> FEATURE:
<223> OTHER INFORMATION: Synthetic Primer

<400> SEQUENCE: 15
caccaccaag ctcccagtat agta                                            24

<210> SEQ ID NO 16
<211> LENGTH: 24
<212> TYPE: DNA
<213> ORGANISM: Artificial Sequence
<220> FEATURE:
<223> OTHER INFORMATION: Synthetic Primer

<400> SEQUENCE: 16
cctcctttct aggtgtacat gctt                                            24

<210> SEQ ID NO 17
<211> LENGTH: 24
<212> TYPE: DNA
<213> ORGANISM: Artificial Sequence
<220> FEATURE:
<223> OTHER INFORMATION: Synthetic Primer

<400> SEQUENCE: 17
atcatggatc ccatgtctct ctat                                            24

<210> SEQ ID NO 18
<211> LENGTH: 24
<212> TYPE: DNA
<213> ORGANISM: Artificial Sequence
<220> FEATURE:
<223> OTHER INFORMATION: Synthetic Primer

<400> SEQUENCE: 18
ttgttcttgg acatgattgg taat                                            24

<210> SEQ ID NO 19
<211> LENGTH: 24
<212> TYPE: DNA
<213> ORGANISM: Artificial Sequence
<220> FEATURE:
<223> OTHER INFORMATION: Synthetic Primer

<400> SEQUENCE: 19
ttcaatgaca aatgaacaaa caaa                                            24

<210> SEQ ID NO 20
<211> LENGTH: 24
<212> TYPE: DNA
<213> ORGANISM: Artificial Sequence

```
<220> FEATURE:
<223> OTHER INFORMATION: Synthetic Primer

<400> SEQUENCE: 20
gaaatcacat ctggaatgtg aaag                                          24

<210> SEQ ID NO 21
<211> LENGTH: 25
<212> TYPE: DNA
<213> ORGANISM: Artificial Sequence
<220> FEATURE:
<223> OTHER INFORMATION: Synthetic Primer

<400> SEQUENCE: 21
aataatgtgt tgttgtcttc caagt                                         25

<210> SEQ ID NO 22
<211> LENGTH: 24
<212> TYPE: DNA
<213> ORGANISM: Artificial Sequence
<220> FEATURE:
<223> OTHER INFORMATION: Synthetic Primer

<400> SEQUENCE: 22
gaaatcacat ctggaatgtg aaag                                          24

<210> SEQ ID NO 23
<211> LENGTH: 22
<212> TYPE: DNA
<213> ORGANISM: Artificial Sequence
<220> FEATURE:
<223> OTHER INFORMATION: Synthetic Primer

<400> SEQUENCE: 23
gttcaagaac agcctcagga ag                                            22

<210> SEQ ID NO 24
<211> LENGTH: 24
<212> TYPE: DNA
<213> ORGANISM: Artificial Sequence
<220> FEATURE:
<223> OTHER INFORMATION: Synthetic Primer

<400> SEQUENCE: 24
ggtgaacact taaatgcgag atag                                          24

<210> SEQ ID NO 25
<211> LENGTH: 24
<212> TYPE: DNA
<213> ORGANISM: Artificial Sequence
<220> FEATURE:
<223> OTHER INFORMATION: Synthetic Primer

<400> SEQUENCE: 25 ttatggggc aaagttttat ttta                                           24

<210> SEQ ID NO 26
<211> LENGTH: 27
<212> TYPE: DNA
<213> ORGANISM: Artificial Sequence
<220> FEATURE:
<223> OTHER INFORMATION: Synthetic Primer

<400> SEQUENCE: 26
tccataaata agtaaaacaa gtgacaa                                       27
```

```
<210> SEQ ID NO 27
<211> LENGTH: 24
<212> TYPE: DNA
<213> ORGANISM: Artificial Sequence
<220> FEATURE:
<223> OTHER INFORMATION: Synthetic Primer

<400> SEQUENCE: 27
ccacttacca cactttcttt gttg                                           24

<210> SEQ ID NO 28
<211> LENGTH: 24
<212> TYPE: DNA
<213> ORGANISM: Artificial Sequence
<220> FEATURE:
<223> OTHER INFORMATION: Synthetic Primer

<400> SEQUENCE: 28
tcattttcag ttgcatgatt ctaa                                           24

<210> SEQ ID NO 29
<211> LENGTH: 24
<212> TYPE: DNA
<213> ORGANISM: Artificial Sequence
<220> FEATURE:
<223> OTHER INFORMATION: Synthetic Primer

<400> SEQUENCE: 29
cagaagtatc aaagcatgta cacc                                           24

<210> SEQ ID NO 30
<211> LENGTH: 25
<212> TYPE: DNA
<213> ORGANISM: Artificial Sequence
<220> FEATURE:
<223> OTHER INFORMATION: Synthetic Primer

<400> SEQUENCE: 30
caacatgttg gtaatggtgc aggga                                          25

<210> SEQ ID NO 31
<211> LENGTH: 21
<212> TYPE: DNA
<213> ORGANISM: Artificial Sequence
<220> FEATURE:
<223> OTHER INFORMATION: Synthetic Primer

<400> SEQUENCE: 31
cgaacaatca tgcataacca a                                              21

<210> SEQ ID NO 32
<211> LENGTH: 24
<212> TYPE: DNA
<213> ORGANISM: Artificial Sequence
<220> FEATURE:
<223> OTHER INFORMATION: Synthetic Primer

<400> SEQUENCE: 32
tgcatgattg ttcgttcata tgtt                                           24

<210> SEQ ID NO 33
<211> LENGTH: 24
<212> TYPE: DNA
<213> ORGANISM: Artificial Sequence
<220> FEATURE:
<223> OTHER INFORMATION: Synthetic Primer

<400> SEQUENCE: 33
```

```
tgacataaag gcataaagac acat                                              24

<210> SEQ ID NO 34
<211> LENGTH: 24
<212> TYPE: DNA
<213> ORGANISM: Artificial Sequence
<220> FEATURE:
<223> OTHER INFORMATION: Synthetic Primer

<400> SEQUENCE: 34
gatgtgaatt tcatgaagtg gttc                                              24

<210> SEQ ID NO 35
<211> LENGTH: 23
<212> TYPE: DNA
<213> ORGANISM: Artificial Sequence
<220> FEATURE:
<223> OTHER INFORMATION: Synthetic Primer

<400> SEQUENCE: 35
ggacttggac atgtgttaac ctc                                               23

<210> SEQ ID NO 36
<211> LENGTH: 24
<212> TYPE: DNA
<213> ORGANISM: Artificial Sequence
<220> FEATURE:
<223> OTHER INFORMATION: Synthetic Primer

<400> SEQUENCE: 36
tatttgcaac ctacaccgaa gtaa                                              24

<210> SEQ ID NO 37
<211> LENGTH: 26
<212> TYPE: DNA
<213> ORGANISM: Artificial Sequence
<220> FEATURE:
<223> OTHER INFORMATION: Synthetic Primer

<400> SEQUENCE: 37
acatggagta agtttctacc ttcttt                                            26

<210> SEQ ID NO 38
<211> LENGTH: 24
<212> TYPE: DNA
<213> ORGANISM: Artificial Sequence
<220> FEATURE:
<223> OTHER INFORMATION: Synthetic Primer

<400> SEQUENCE: 38
tatttgcaac ctacaccgaa gtaa                                              24

<210> SEQ ID NO 39
<211> LENGTH: 26
<212> TYPE: DNA
<213> ORGANISM: Artificial Sequence
<220> FEATURE:
<223> OTHER INFORMATION: Synthetic Primer

<400> SEQUENCE: 39
acatggagta agtttctacc ttcttt                                            26

<210> SEQ ID NO 40
<211> LENGTH: 27
<212> TYPE: DNA
<213> ORGANISM: Artificial Sequence
```

```
<220> FEATURE:
<223> OTHER INFORMATION: Synthetic Primer

<400> SEQUENCE: 40
tttctcctat tctacaatca ataatcc                                              27

<210> SEQ ID NO 41
<211> LENGTH: 27
<212> TYPE: DNA
<213> ORGANISM: Artificial Sequence
<220> FEATURE:
<223> OTHER INFORMATION: Synthetic Primer

<400> SEQUENCE: 41
aaagtaagtg catttctagc ataattt                                              27

<210> SEQ ID NO 42
<211> LENGTH: 25
<212> TYPE: DNA
<213> ORGANISM: Artificial Sequence
<220> FEATURE:
<223> OTHER INFORMATION: Synthetic Primer

<400> SEQUENCE: 42
aagatttcat tcttcctctt ctagg                                                25

<210> SEQ ID NO 43
<211> LENGTH: 23
<212> TYPE: DNA
<213> ORGANISM: Artificial Sequence
<220> FEATURE:
<223> OTHER INFORMATION: Synthetic Primer

<400> SEQUENCE: 43
aattgaggaa tgcaagatgt gtc                                                  23

<210> SEQ ID NO 44
<211> LENGTH: 24
<212> TYPE: DNA
<213> ORGANISM: Artificial Sequence
<220> FEATURE:
<223> OTHER INFORMATION: Synthetic Primer

<400> SEQUENCE: 44
acacatcttg cattcctcaa ttct                                                 24

<210> SEQ ID NO 45
<211> LENGTH: 24
<212> TYPE: DNA
<213> ORGANISM: Artificial Sequence
<220> FEATURE:
<223> OTHER INFORMATION: Synthetic Primer

<400> SEQUENCE: 45
ctttctggct cacggtaata ctct                                                 24

<210> SEQ ID NO 46
<211> LENGTH: 24
<212> TYPE: DNA
<213> ORGANISM: Artificial Sequence
<220> FEATURE:
<223> OTHER INFORMATION: Synthetic Primer

<400> SEQUENCE: 46
ttcttggaga gtattaccgt gagc                                                 24
```

```
<210> SEQ ID NO 47
<211> LENGTH: 25
<212> TYPE: DNA
<213> ORGANISM: Artificial Sequence
<220> FEATURE:
<223> OTHER INFORMATION: Synthetic Primer

<400> SEQUENCE: 47
caatatttat taattaccac cttac                                          25

<210> SEQ ID NO 48
<211> LENGTH: 22
<212> TYPE: DNA
<213> ORGANISM: Artificial Sequence
<220> FEATURE:
<223> OTHER INFORMATION: Synthetic Primer

<400> SEQUENCE: 48
ctaggttatt acgcaccacc ca                                             22

<210> SEQ ID NO 49
<211> LENGTH: 24
<212> TYPE: DNA
<213> ORGANISM: Artificial Sequence
<220> FEATURE:
<223> OTHER INFORMATION: Synthetic Primer

<400> SEQUENCE: 49
ggaggagcac tgggatcaaa agct                                           24

<210> SEQ ID NO 50
<211> LENGTH: 28
<212> TYPE: DNA
<213> ORGANISM: Artificial Sequence
<220> FEATURE:
<223> OTHER INFORMATION: Synthetic Primer

<400> SEQUENCE: 50
cacactaagc caaagccaaa gcagcaat                                       28

<210> SEQ ID NO 51
<211> LENGTH: 24
<212> TYPE: DNA
<213> ORGANISM: Artificial Sequence
<220> FEATURE:
<223> OTHER INFORMATION: Synthetic Primer

<400> SEQUENCE: 51
agcactggga tcaaaagctt cctt                                           24

<210> SEQ ID NO 52
<211> LENGTH: 23
<212> TYPE: DNA
<213> ORGANISM: Artificial Sequence
<220> FEATURE:
<223> OTHER INFORMATION: Synthetic Primer

<400> SEQUENCE: 52
aataatggat accaaaagga agc                                            23

<210> SEQ ID NO 53
<211> LENGTH: 24
<212> TYPE: DNA
<213> ORGANISM: Artificial Sequence
<220> FEATURE:
<223> OTHER INFORMATION: Synthetic Primer

<400> SEQUENCE: 53
```
gttgaagtga cttgcagcag ccat          24

<210> SEQ ID NO 54
<211> LENGTH: 24
<212> TYPE: DNA
<213> ORGANISM: Artificial Sequence
<220> FEATURE:
<223> OTHER INFORMATION: Synthetic Primer

<400> SEQUENCE: 54
atggatacca aaggaagct tttg           24

<210> SEQ ID NO 55
<211> LENGTH: 27
<212> TYPE: DNA
<213> ORGANISM: Artificial Sequence
<220> FEATURE:
<223> OTHER INFORMATION: Synthetic Primer

<400> SEQUENCE: 55
gatagataag catagaaaac atggtaa       27

<210> SEQ ID NO 56
<211> LENGTH: 26
<212> TYPE: DNA
<213> ORGANISM: Artificial Sequence
<220> FEATURE:
<223> OTHER INFORMATION: Synthetic Primer

<400> SEQUENCE: 56
actgtgttgg gttaccatgt tttcta        26

<210> SEQ ID NO 57
<211> LENGTH: 24
<212> TYPE: DNA
<213> ORGANISM: Artificial Sequence
<220> FEATURE:
<223> OTHER INFORMATION: Synthetic Primer

<400> SEQUENCE: 57
caataaataa cccaaaaatt gaaa          24

<210> SEQ ID NO 58
<211> LENGTH: 23
<212> TYPE: DNA
<213> ORGANISM: Artificial Sequence
<220> FEATURE:
<223> OTHER INFORMATION: Synthetic Primer

<400> SEQUENCE: 58
gcaatatcaa cactgtgttg ggt           23

<210> SEQ ID NO 59
<211> LENGTH: 27
<212> TYPE: DNA
<213> ORGANISM: Artificial Sequence
<220> FEATURE:
<223> OTHER INFORMATION: Synthetic Primer

<400> SEQUENCE: 59
ctagaatcca ataaataacc caaaaat       27

<210> SEQ ID NO 60
<211> LENGTH: 24
<212> TYPE: DNA
<213> ORGANISM: Artificial Sequence

```
<220> FEATURE:
<223> OTHER INFORMATION: Synthetic Primer

<400> SEQUENCE: 60
gagtttcaat ttttgggtta ttta                                        24

<210> SEQ ID NO 61
<211> LENGTH: 24
<212> TYPE: DNA
<213> ORGANISM: Artificial Sequence
<220> FEATURE:
<223> OTHER INFORMATION: Synthetic Primer

<400> SEQUENCE: 61
ccattgaggc ccactatgaa ttcc                                        24

<210> SEQ ID NO 62
<211> LENGTH: 19
<212> TYPE: DNA
<213> ORGANISM: Artificial Sequence
<220> FEATURE:
<223> OTHER INFORMATION: Synthetic Primer

<400> SEQUENCE: 62
gagtttcaat ttttgggtt                                              19

<210> SEQ ID NO 63
<211> LENGTH: 26
<212> TYPE: DNA
<213> ORGANISM: Artificial Sequence
<220> FEATURE:
<223> OTHER INFORMATION: Synthetic Primer

<400> SEQUENCE: 63
tccattgagg cccactatga attcct                                      26

<210> SEQ ID NO 64
<211> LENGTH: 25
<212> TYPE: DNA
<213> ORGANISM: Artificial Sequence
<220> FEATURE:
<223> OTHER INFORMATION: Synthetic Primer

<400> SEQUENCE: 64
gacaggaatt catagtgggc ctcaa                                       25

<210> SEQ ID NO 65
<211> LENGTH: 27
<212> TYPE: DNA
<213> ORGANISM: Artificial Sequence
<220> FEATURE:
<223> OTHER INFORMATION: Synthetic Primer

<400> SEQUENCE: 65
ctgacaattc aatatttatt aattacc                                     27

<210> SEQ ID NO 66
<211> LENGTH: 26
<212> TYPE: DNA
<213> ORGANISM: Artificial Sequence
<220> FEATURE:
<223> OTHER INFORMATION: Synthetic Primer

<400> SEQUENCE: 66
atacttcaga taaagctgtt cttgaa                                      26
```

<210> SEQ ID NO 67
<211> LENGTH: 27
<212> TYPE: DNA
<213> ORGANISM: Artificial Sequence
<220> FEATURE:
<223> OTHER INFORMATION: Synthetic Primer

<400> SEQUENCE: 67
ttgtgatact agttaagacc cataaaa                                        27

<210> SEQ ID NO 68
<211> LENGTH: 23
<212> TYPE: DNA
<213> ORGANISM: Artificial Sequence
<220> FEATURE:
<223> OTHER INFORMATION: Synthetic Primer

<400> SEQUENCE: 68
gataaagctg ttcttgaaca ttt                                            23

<210> SEQ ID NO 69
<211> LENGTH: 27
<212> TYPE: DNA
<213> ORGANISM: Artificial Sequence
<220> FEATURE:
<223> OTHER INFORMATION: Synthetic Primer

<400> SEQUENCE: 69
tttttgtgat actagttaag acccata                                        27

<210> SEQ ID NO 70
<211> LENGTH: 22
<212> TYPE: DNA
<213> ORGANISM: Artificial Sequence
<220> FEATURE:
<223> OTHER INFORMATION: Synthetic Primer

<400> SEQUENCE: 70
tttgtcatta tcttagttaa cc                                             22

<210> SEQ ID NO 71
<211> LENGTH: 27
<212> TYPE: DNA
<213> ORGANISM: Artificial Sequence
<220> FEATURE:
<223> OTHER INFORMATION: Synthetic Primer

<400> SEQUENCE: 71
aaaaagagga aaagtaatg taagagt                                         27

<210> SEQ ID NO 72
<211> LENGTH: 27
<212> TYPE: DNA
<213> ORGANISM: Artificial Sequence
<220> FEATURE:
<223> OTHER INFORMATION: Synthetic Primer

<400> SEQUENCE: 72
cattaattat gtaattgttt gaacacg                                        27

<210> SEQ ID NO 73
<211> LENGTH: 24
<212> TYPE: DNA
<213> ORGANISM: Artificial Sequence
<220> FEATURE:
<223> OTHER INFORMATION: Synthetic Primer

<400> SEQUENCE: 73

```
aaaccacatc tccagtgtca ctta                                          24
```

<210> SEQ ID NO 74
<211> LENGTH: 24
<212> TYPE: DNA
<213> ORGANISM: Artificial Sequence
<220> FEATURE:
<223> OTHER INFORMATION: Synthetic Primer

<400> SEQUENCE: 74

```
tcacttacga agtggtcttg tctc                                          24
```

<210> SEQ ID NO 75
<211> LENGTH: 25
<212> TYPE: DNA
<213> ORGANISM: Artificial Sequence
<220> FEATURE:
<223> OTHER INFORMATION: Synthetic Primer

<400> SEQUENCE: 75

```
tttgaatatt tcaattctcc aatta                                         25
```

<210> SEQ ID NO 76
<211> LENGTH: 24
<212> TYPE: DNA
<213> ORGANISM: Artificial Sequence
<220> FEATURE:
<223> OTHER INFORMATION: Synthetic Primer

<400> SEQUENCE: 76

```
gttattgatc caaccatagt cacg                                          24
```

<210> SEQ ID NO 77
<211> LENGTH: 27
<212> TYPE: DNA
<213> ORGANISM: Artificial Sequence
<220> FEATURE:
<223> OTHER INFORMATION: Synthetic Primer

<400> SEQUENCE: 77

```
cattaattat gtaattgttt gaacacg                                       27
```

<210> SEQ ID NO 78
<211> LENGTH: 24
<212> TYPE: DNA
<213> ORGANISM: Artificial Sequence
<220> FEATURE:
<223> OTHER INFORMATION: Synthetic Primer

<400> SEQUENCE: 78

```
gaggtgataa tgaggaattt gagg                                          24
```

<210> SEQ ID NO 79
<211> LENGTH: 24
<212> TYPE: DNA
<213> ORGANISM: Artificial Sequence
<220> FEATURE:
<223> OTHER INFORMATION: Synthetic Primer

<400> SEQUENCE: 79

```
tatttgttat gtggctggac tttg                                          24
```

<210> SEQ ID NO 80
<211> LENGTH: 24

```
<212> TYPE: DNA
<213> ORGANISM: Artificial Sequence
<220> FEATURE:
<223> OTHER INFORMATION: Synthetic Primer

<400> SEQUENCE: 80
aaaccacatc tccagtgtca ctta                                           24

<210> SEQ ID NO 81
<211> LENGTH: 24
<212> TYPE: DNA
<213> ORGANISM: Artificial Sequence
<220> FEATURE:
<223> OTHER INFORMATION: Synthetic Primer

<400> SEQUENCE: 81
actttgtcac atacttgcat cacc                                           24

<210> SEQ ID NO 82
<211> LENGTH: 24
<212> TYPE: DNA
<213> ORGANISM: Artificial Sequence
<220> FEATURE:
<223> OTHER INFORMATION: Synthetic Primer

<400> SEQUENCE: 82
tcacttacga agtggtcttg tctc                                           24

<210> SEQ ID NO 83
<211> LENGTH: 26
<212> TYPE: DNA
<213> ORGANISM: Artificial Sequence
<220> FEATURE:
<223> OTHER INFORMATION: Synthetic Primer

<400> SEQUENCE: 83
agaaatcgca tctggaatgt gaaagt                                         26

<210> SEQ ID NO 84
<211> LENGTH: 26
<212> TYPE: DNA
<213> ORGANISM: Artificial Sequence
<220> FEATURE:
<223> OTHER INFORMATION: Synthetic Primer

<400> SEQUENCE: 84
tgggtttcct agcacgctat aaaaat                                         26

<210> SEQ ID NO 85
<211> LENGTH: 15
<212> TYPE: DNA
<213> ORGANISM: Artificial Sequence
<220> FEATURE:
<223> OTHER INFORMATION: Synthetic Primer

<400> SEQUENCE: 85
caacgacaga tgaag                                                     15

<210> SEQ ID NO 86
<211> LENGTH: 15
<212> TYPE: DNA
<213> ORGANISM: Artificial Sequence
<220> FEATURE:
<223> OTHER INFORMATION: Synthetic Primer

<400> SEQUENCE: 86
caacgacaaa tgaag                                                     15
```

<210> SEQ ID NO 87
<211> LENGTH: 33
<212> TYPE: DNA
<213> ORGANISM: Artificial Sequence
<220> FEATURE:
<223> OTHER INFORMATION: Synthetic Primer

<400> SEQUENCE: 87
agaaacttac tccatgttac tctgtctata tgt                          33

<210> SEQ ID NO 88
<211> LENGTH: 30
<212> TYPE: DNA
<213> ORGANISM: Artificial Sequence
<220> FEATURE:
<223> OTHER INFORMATION: Synthetic Primer

<400> SEQUENCE: 88
ttgtgaaata gagaattaat accgcttcga                              30

<210> SEQ ID NO 89
<211> LENGTH: 18
<212> TYPE: DNA
<213> ORGANISM: Artificial Sequence
<220> FEATURE:
<223> OTHER INFORMATION: Synthetic Primer

<400> SEQUENCE: 89
aaaggtgatg gataacat                                           18

<210> SEQ ID NO 90
<211> LENGTH: 19
<212> TYPE: DNA
<213> ORGANISM: Artificial Sequence
<220> FEATURE:
<223> OTHER INFORMATION: Synthetic Primer

<400> SEQUENCE: 90
aaaaggtaat ggataacat                                          19

<210> SEQ ID NO 91
<211> LENGTH: 24
<212> TYPE: DNA
<213> ORGANISM: Artificial Sequence
<220> FEATURE:
<223> OTHER INFORMATION: Synthetic Primer

<400> SEQUENCE: 91
ggtggtctta caacagtaga tcgc                                    24

<210> SEQ ID NO 92
<211> LENGTH: 28
<212> TYPE: DNA
<213> ORGANISM: Artificial Sequence
<220> FEATURE:
<223> OTHER INFORMATION: Synthetic Primer

<400> SEQUENCE: 92
ccgcttcgat taaatgataa tgtggaat                                28

<210> SEQ ID NO 93
<211> LENGTH: 18
<212> TYPE: DNA
<213> ORGANISM: Artificial Sequence
<220> FEATURE:
<223> OTHER INFORMATION: Synthetic Primer

```
<400> SEQUENCE: 93
aaaggtgatg gataacat                                                    18

<210> SEQ ID NO 94
<211> LENGTH: 19
<212> TYPE: DNA
<213> ORGANISM: Artificial Sequence
<220> FEATURE:
<223> OTHER INFORMATION: Synthetic Primer

<400> SEQUENCE: 94
aaaaggtaat ggataacat                                                   19

<210> SEQ ID NO 95
<211> LENGTH: 25
<212> TYPE: DNA
<213> ORGANISM: Artificial Sequence
<220> FEATURE:
<223> OTHER INFORMATION: Synthetic Primer

<400> SEQUENCE: 95 ccggctttttt tgtttgtcat tggaa                                           25

<210> SEQ ID NO 96
<211> LENGTH: 32
<212> TYPE: DNA
<213> ORGANISM: Artificial Sequence
<220> FEATURE:
<223> OTHER INFORMATION: Synthetic Primer

<400> SEQUENCE: 96
tcaagatgta tttcattatt ttctgaaacg cg                                    32

<210> SEQ ID NO 97
<211> LENGTH: 26
<212> TYPE: DNA
<213> ORGANISM: Artificial Sequence
<220> FEATURE:
<223> OTHER INFORMATION: Synthetic Primer

<400> SEQUENCE: 97
ctataaaaat tgaatcaata gaagaa                                           26

<210> SEQ ID NO 98
<211> LENGTH: 22
<212> TYPE: DNA
<213> ORGANISM: Artificial Sequence
<220> FEATURE:
<223> OTHER INFORMATION: Synthetic Primer

<400> SEQUENCE: 98
aaaaattgaa tcaataaaag aa                                               22
```

HIGH YIELDING SOYBEAN PLANTS WITH LOW LINOLENIC ACID

This application is a division of U.S. application Ser. No. 11/239,676, filed Sep. 29, 2008, now U.S. Pat. No. 7,442,850 which claims the priority of U.S. Provisional Patent Appl. Ser. No. 60/614,331, filed Sep. 29, 2004, the entire disclosures of which are specifically incorporated herein by reference.

BACKGROUND OF THE INVENTION

1. Field of the Invention

The present invention relates generally to the field of plant breeding. In particular, the invention relates to agronomically elite soybean varieties with commercially significant yield and a mid/low-linolenic acid content.

2. Description of Related Art

Soybean seeds are an important source of vegetable oil, which is used in food products throughout the world. The relatively high level (usually about 8%) of linolenic acid (18:3) in soybean oil reduces its stability and flavor.

Hydrogenation of soybean oil is used to lower the level of linolenic acid (18:3) and improve both stability and flavor of soybean oils (Dutton et al., 1951; Lui and White, 1992). However, hydrogenation results in the production of trans fatty acids, which increases the risk for coronary heart disease when consumed (Hu et al., 1997).

Varieties of low linolenic acid soybean have been produced through mutation, screening and breeding (Fehr et al., 1992; Rahman and Takagi, 1997; Ross et al., 2000; Byrum et al., 1997; Stoisin et al., 1998). Varieties with a linolenic acid content on the order of 1% or lower in particular have been produced (U.S. Pat. Nos. 5,534,425 and 5,714,670). However, the low linolenic acid lines produced to date have been plagued poor seed yield and other agronomic characteristics desired for commercial production. The problem has been difficult to solve and is complicated by the quantitative nature of agronomic traits such as linolenic acid content and yield. The usefulness of low linolenic acid content soybean has therefore been limited in most commercial settings.

Developing a product with commercially significance seed yield is a high priority in most soybean cultivar development programs. Yield is controlled by many genes and strongly influenced by the environment. It is a characteristic of central importance to the commercial value of a variety and breeders continually attempt to improve yield beyond that presently available. It is a difficult challenge to incorporate low linolenic acid content into high yielding cultivars.

Likely because of the difficulty, the prior art has failed to provide high yielding soybean varieties that also posses low linolenic acid and agronomically elite characteristics. However, there is a great need in the art for such soybean plants. The Food and Drug Administration (FDA) has proposed regulations on nutrition labeling to require that the amount of trans fatty acids in a food be included in the Nutrition Facts panel. In addition to the health benefits of reducing our reliance on hydrogenation of soybean oils, the aforementioned proposal by FDA has sparked great interest in the production of low linolenic acid (less than 3%) soybean that does not require, or requires less hydrogenation. Decreased linolenic acid can significantly improve the value of a soybean harvest. For the decreased linolenic acid to have commercial significance, yield and/or elite agronomic traits must not be substantially impacted. Therefore, providing soybean plants that are agronomically elite while both high yielding and possessing decreased linolenic acid would represent a substantial advance in the art and benefit farmers and consumers alike.

SUMMARY OF THE INVENTION

In one aspect, the invention provides a soybean plant of an agronomically elite variety having a mid/low-linolenic acid content and a commercially significant yield. Also provided are the parts of this plant, including, but not limited to, pollen, an ovule, a cell and a seed. Further provided is a tissue culture of regenerable cells of the plant, wherein the tissue culture regenerates soybean plants capable of expressing all the physiological and morphological characteristics of the plant. In one embodiment of the invention, the regenerable cells are embryos, meristematic cells, pollen, leaves, roots, root tips or flowers or are protoplasts or callus derived therefrom. Further provided by the invention is a soybean plant regenerated from the tissue culture capable of expressing all the physiological and morphological characteristics of the starting plant.

In certain embodiments of the invention, a mid/low-linolenic acid content is defined as a linolenic acid content of from about 1.0% to about 3.0% by weight of total seed fatty acids, including from about 1.5% to about 3.0%, about 2% to about 2.6%, about 2% to about 3%, about 1% to about 2.6%, about 1% to about 2.2%, about 1.6% to about 2.6% and about 2% to about 2.4% by weight of total seed fatty acids. Such plants may further be defined as having a grain yield of, for example, at least about 90%, 94%, 98%, 100%, 103% 105% or about 110% of the check lines AG2703 and DKB23-51. Line AG2703, which also has the designations SN79553 and 9323265446452, was patented in U.S. Pat. No. 6,184,442, the disclosure of which is incorporated herein by reference in its entirety. The line designated DKB23-51, which also has the designations 02122920 and 958361722350, was patented in U.S. Pat. No. 6,369,302, the disclosure of which is incorporated herein by reference in its entirety. Seeds of AG2703 and DKB23-51 have been deposited with the ATCC under ATCC accession numbers PTA-2577 and PTA-3933, respectively.

In yet another aspect, the invention provides plant parts of a plant of the invention. Examples of such parts include pollen, an ovule, a meristem or a cell. The invention also provides seeds of a plant described herein, as well as tissue cultures comprising cells of such a plant, wherein the tissue culture regenerates soybean plants expressing the physiological and morphological characteristics of the plant. The tissue culture may be comprised of regenerable cells such as embryos, meristematic cells, pollen, leaves, roots, root tips or flowers.

In still another aspect, the invention provides a soybean plant of the invention comprising a transgene. The transgene may in one embodiment be defined as conferring a trait selected from the group consisting of herbicide tolerance; disease resistance; insect or pest resistance; altered fatty acid, protein or carbohydrate metabolism; increased grain yield; altered plant maturity, and altered morphological characteristics. One example of herbicide resistance is glyphosate resistance.

In particular embodiments, a plant of the invention may be further defined as produced by a method comprising the steps of: a) crossing first and second soybean plants, wherein the plants comprise Fad3-1b and Fad3-1c alleles conferring decreased linolenic acid content, wherein the first plant has a mid/low-linolenic acid content, and wherein the second plant comprises a commercially significant yield; b) assaying progeny soybean plants resulting from the crossing for yield and for the presence of polymorphisms located in a soybean plant genomic region within 50 cM of said Fad3-1b and Fad3-1c alleles; and c) selecting at least a first agronomically elite progeny plant comprising said polymorphisms and a commercially significant yield to obtain the plant of claim 1.

In still yet another aspect, the invention provides a method of obtaining soybean germplasm, comprising the steps of: a) identifying at least a first polymorphism in a soybean plant genomic region within 50 cM of a Fad3-1b or Fad3-1c allele conferring decreased linolenic acid content; b) assaying soybean plants for the presence of the polymorphism; and c) selecting at least a first soybean plant comprising the polymorphism. The method may comprise identifying polymorphisms in a soybean plant genomic region within 50 cM of both of said Fad3-1b and Fad3-1c alleles and assaying for the presence of said polymorphisms. In one embodiment, the first polymorphism comprises a single nucleotide polymorphism at a position in the Fad3-1b gene sequence corresponding to nucleotide 2021 of SEQ ID NO:1. In another embodiment, the first polymorphism comprises a single nucleotide polymorphism at a position in the Fad3-1c gene sequence corresponding to nucleotide 687, 1129, 1203, 2316, 3292, 3360 or 3743 of SEQ ID NO:2. The first polymorphism may also comprise a deletion in the Fad3-1c gene sequence, and may comprise a polymorphism in the Fad3-1c promoter, such as a single nucleotide polymorphism at a position corresponding to nucleotide 334, 364, 385, 387, 393, 729 or 747 of SEQ ID NO:3. Detecting the polymorphism may be carried out by any method, including PCR, single strand conformational polymorphism analysis, denaturing gradient gel electrophoresis, cleavage fragment length polymorphism analysis and/or DNA sequencing.

In still yet another aspect, the invention provides a method of plant breeding comprising the steps of: a) assaying soybean plants for the presence of at least a first polymorphism in a soybean plant genomic region within 50 cM of a Fad3-1b or Fad3-1c allele conferring decreased linolenic acid content; b) selecting at least a first soybean plant comprising the polymorphism; and c) crossing the first soybean plant to a second soybean plant to produce progeny plants comprising the polymorphism. The method may further comprise the step of: d) selecting a progeny plant comprising the polymorphism and crossing the progeny plant with a third soybean plant to produce additional progeny plants. In the method the second and third plants may be of the same variety. In certain embodiments, the method further comprises repeating step d) about 2-10 times. The method may still further comprise assaying soybean plants for the presence of polymorphisms in soybean plant genomic regions within 50 cM of said Fad3-1b and Fad3-1c alleles and selecting said first soybean plant may be based on the presence of the polymorphisms. In certain embodiments, markers linked to Fad3-1b and Fad3-1c may be assayed without assaying for markers tightly linked to Fad3-1a, as the inventors have shown that it is the Fad3-1b and Fad3-1c alleles that contribute a low linolenic acid content.

In certain embodiments of the method, the first polymorphism comprises a single nucleotide polymorphism at a position in the Fad3-1b gene corresponding to nucleotide 2021 of SEQ ID NO:1. The first polymorphism may also comprise a single nucleotide polymorphism at a position in the Fad3-1c gene corresponding to nucleotide 687, 1129, 1203, 2316, 3292, 3360 or 3743 of SEQ ID NO:2. In still other embodiments the first polymorphism comprises a deletion in the Fad3-1c gene sequence and/or a single nucleotide polymorphism at a position in the Fad3-1c promoter corresponding to nucleotide 334, 364, 385, 387, 393, 729 or 747 of SEQ ID NO:3. Selecting at least a first soybean plant comprising the polymorphism may be carried out by any method, such as, for example, PCR, single strand conformational polymorphism analysis, denaturing gradient gel electrophoresis, cleavage fragment length polymorphism analysis and/or DNA sequencing.

In still yet another aspect, the invention provides a probe or primer that hybridizes under stringent conditions to a soybean plant genomic region within 50 cM of a Fad3-1b or Fad3-1c allele, wherein the probe or primer is a nucleic acid sequence selected from the group consisting SEQ ID NOs:4-98.

Still yet another aspect of the invention is a method of producing a food product for human or animal consumption comprising: (a) obtaining a plant of the invention; (b) cultivating the plant to maturity; and (c) preparing a food product from the plant. In certain embodiments of the invention, the food product may be protein concentrate, protein isolate, meal, oil, flour or soybean hulls.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein:

FIG. 1A shows the allelogram of NS0193117. The allelic patterns from the Taqman assay were consistent with the sequences. FIG. 1B shows the allelogram of NS0193115 on the sequencing panel. All four lines with low linolenic content had a different allele from the wild-type, corresponding well with the sequences. FIG. 1C shows the allelogram of NS0193116, derived from Fad3-1c position 687.

DETAILED DESCRIPTION OF THE INVENTION

Figure 1A:
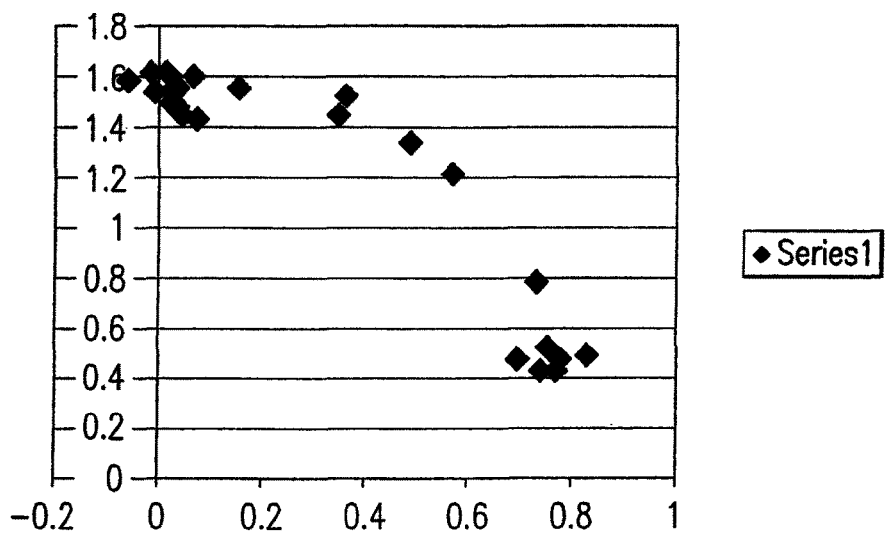
FIG. 1A-C.

The invention overcomes the deficiencies of the prior art by providing agronomically elite soybean varieties with a mid/low-linolenic acid content and commercially acceptable grain yield. The invention is significant in that, although the benefits of these characteristics have been realized individually, they have not previously been combined in a single variety. The provision of a mid/low linolenic acid content in combination with other desirable characteristics provides many benefits. For example, current soybean oils must typically be at least partially hydrogenated and/or mixed with other oils due to problems with oil stability. Reduced linolenic acid content reduces the need for either solution by improving stability and, depending upon use, can eliminate the need for hydrogenation. The cost and quality of soybean oil can therefore be markedly improved by decreasing linolenic acid content, making the oil increasingly competitive relative to other seed oils. Low linolenic acid content also reduces off-flavors and thus lines with this characteristic have higher commercial value (Liu and White, 1992). However, widespread adoption of low-linolenic varieties has to date been hampered by poor yields or agronomic quality.

The invention provides genetic markers and methods for their use for the creation of such improved plants. This is significant because of the complex inheritance of quantitative traits, such as yield and linolenic acid content, which is made exponential when attempting to combine the traits. The markers were identified using the candidate gene approach. Locus-specific nested primers were designed to cover the entire FAD3 gene family consisting of three independent loci.

Amplicons were generated from 25 different genotypes comprising 9 mutants and 16 wild types. SNPs and Indels were identified through sequence alignment. Genetic segregation analysis confirmed that the markers identified linked to the alleles Fad3-1b and Fad3-1c, which were associated with mutations in the corresponding wildtype sequences yielding low linolenic phenotypes. Analysis of the segregating plants demonstrated that Fad3-1b and Fad3-1c additively control linolenic content in soybean. Therefore, using a combination of markers for Fad3-1b and Fad3-1c, the invention allows accurate prediction of linolenic acid content in plants without the need for expensive biochemical analyses. These markers were successfully demonstrated for use in low linolenic soybean breeding programs and allowed, for the first time, the development of soybean varieties combining a low linolenic acid phenotype with commercially significant yield and agronomically elite characteristics.

The prior art has failed to provide plants of such a variety, presumably because of the difficulty in combining different traits with complex inheritance and lack of means for overcoming these difficulties. By describing methods for the production of such plants and providing examples of these plants, the invention now allows the preparation of a potentially unlimited number of novel soybean varieties exhibiting a commercially significant yield with combined with low linolenic acid content and specifically a mid/low linolenic acid content. Once such an elite variety is produced the combined yield and low linolenic acid content can be transferred to other varieties with appropriate backcross and selection to maintain the desirable traits as described herein below.

I. PLANTS OF THE INVENTION

The invention provides for the first time plants and derivatives thereof of soybean varieties that combine commercially significant yield and mid/low-linolenic acid content with an agronomically elite phenotype. Such plants may be defined as having a commercially significant yield, for example, that is defined as a yield of at least 103% of the check lines AG2703 and DKB23-51. In certain further embodiments, plants are provided having a mid/low-linolenic acid content and a grain yield of at least about 90%, 94%, 98%, 100%, 105% or about 110% of these lines. Such plants may be defined, in certain embodiments of the invention, as having a yield a yield in excess of about 35, 37, 39, 41, 43 or 45 bushels per acre over at least 10 environments. In particular embodiments of the invention, the mid/low-linolenic acid content may be defined as from about 1% to about 3% of seed fatty acid content, including from about 1.3% to about 3%, from about 1.5% to about 3%, from about 1.8% to about 3%, from about 2.1% to about 3%, from about 2.4% to about 3%, from about 2.6% to about 3%, from about 1% to about 2.6%, from about 1.3% to about 2.6%, from about 1.8% to about 2.6%, from about 2% to about 2.6%, from about 2% to about 2.4% and from about 1.6% to about 2.4% of seed fatty acid content.

One aspect of the current invention is therefore directed to the aforementioned plants and parts thereof and methods for using these plants and plant parts. Plant parts include, but are not limited to, pollen, an ovule and a cell. The invention further provides tissue cultures of regenerable cells of these plants, which cultures regenerate soybean plants capable of expressing all the physiological and morphological characteristics of the starting variety. Such regenerable cells may include embryos, meristematic cells, pollen, leaves, roots, root tips or flowers, or protoplasts or callus derived therefrom. Also provided by the invention are soybean plants regenerated from such a tissue culture, wherein the plants are capable of expressing all the physiological and morphological characteristics of the starting plant variety from which the regenerable cells were obtained.

II. MARKER ASSISTED SELECTION FOR PRODUCTION OF SOYBEAN VARIETIES WITH MID/LOW-LINOLENIC ACID CONTENT

The current invention provides genetic markers and methods for the introduction of loci conferring a mid/low-linolenic acid content in soybean plants. The invention therefore allows for the first time the creation of plants that combine this linolenic acid content with a commercially significant yield and an agronomically elite genetic background. Using the methods of the invention, loci conferring decreased linolenic acid content may be introduced into potentially any desired soybean genetic background, for example, in the production of new varieties with commercially significant yield and a mid/low-linolenic acid content.

Marker assisted introgression involves the transfer of a chromosome region defined by one or more markers from one germplasm to a second germplasm. The initial step in that process is the localization of the trait by gene mapping, which is the process of determining the position of a gene relative to other genes and genetic markers through linkage analysis. The basic principle for linkage mapping is that the closer together two genes are on the chromosome, the more likely they are to be inherited together. Briefly, a cross is generally made between two genetically compatible but divergent parents relative to traits under study. Genetic markers can then be used to follow the segregation of traits under study in the progeny from the cross, often a backcross (BC1), $F_2$, or recombinant inbred population.

The term quantitative trait loci, or QTL, is used to describe regions of a genome showing qualitative or additive effects upon a phenotype. The current inventors have identified genetic markers for two such QTLs, Fad3-1b and Fad3-1c. The invention therefore allows the use of molecular tools to combine these QTLs with desired characteristics.

A. Development of Linked Genetic Markers

A sample first plant population may be genotyped for an inherited genetic marker to form a genotypic database. As used herein, an "inherited genetic marker" is an allele at a single locus. A locus is a position on a chromosome, and allele refers to conditions of genes; that is, different nucleotide sequences, at those loci. The marker allelic composition of each locus can be either homozygous or heterozygous. In order for information to be gained from a genetic marker in a cross, the marker must by polymorphic; that is, it must exist in different forms so that the chromosome carrying the mutant gene can be distinguished from the chromosome with the normal gene by the form of the marker it also carries.

Formation of a phenotypic database can be accomplished by making direct observations of one or more traits on progeny derived from artificial or natural self-pollination of a sample plant or by quantitatively assessing the combining ability of a sample plant. By way of example, a plant line may be crossed to, or by, one or more testers. Testers can be inbred lines, single, double, or multiple cross hybrids, or any other assemblage of plants produced or maintained by controlled or free mating, or any combination thereof. For some self-pollinating plants, direct evaluation without progeny testing is preferred.

The marker genotypes may be determined in the testcross generation and the marker loci mapped. To map a particular trait by the linkage approach, it is necessary to establish a positive correlation in inheritance of a specific chromosomal locus with the inheritance of the trait. In the case of complex inheritance, such as with as quantitative traits, including specifically linolenic acid content and yield, linkage will generally be much more difficult to discern. In this case, statistical procedures may be needed to establish the correlation between phenotype and genotype. This may further necessitate examination of many offspring from a particular cross, as individual loci may have small contributions to an overall phenotype.

Coinheritance, or genetic linkage, of a particular trait and a marker suggests that they are physically close together on the chromosome. Linkage is determined by analyzing the pattern of inheritance of a gene and a marker in a cross. The unit of recombination is the centimorgan (cM). Two markers are one centimorgan apart if they recombine in meiosis once in every 100 opportunities that they have to do so. The centimorgan is a genetic measure, not a physical one. Those markers located less then 50 cM from a second locus are said to be genetically linked, because they are not inherited independently of one another. Thus, the percent of recombination observed between the loci per generation will be less than 50%. In particular embodiments of the invention, markers may be used located less than about 45, 35, 25, 15, 10, 5, 4, 3, 2, or 1 or less cM apart on a chromosome. In certain embodiments of the invention markers may be used detecting polymorphisms within the contributing loci themselves and thus located at 0 cM respective to the loci, for example, comprising a mutation within a Fad3-1b or Fad3-1c coding sequence or regulatory element.

During meiosis, pairs of homologous chromosomes come together and exchange segments in a process called recombination. The further a marker is from a gene, the more chance there is that there will be recombination between the gene and the marker. In a linkage analysis, the coinheritance of marker and gene or trait are followed in a particular cross. The probability that their observed inheritance pattern could occur by chance alone, i.e., that they are completely unlinked, is calculated. The calculation is then repeated assuming a particular degree of linkage, and the ratio of the two probabilities (no linkage versus a specified degree of linkage) is determined. This ratio expresses the odds for (and against) that degree of linkage, and because the logarithm of the ratio is used, it is known as the logarithm of the odds, e.g. an lod score. A lod score equal to or greater than 3, for example, is taken to confirm that gene and marker are linked. This represents 1000:1 odds that the two loci are linked. Calculations of linkage is greatly facilitated by use of statistical analysis employing programs.

The genetic linkage of marker molecules can be established by a gene mapping model such as, without limitation, the flanking marker model reported by Lander and Botstein (1989), and the interval mapping, based on maximum likelihood methods described by Lander and Botstein (1989), and implemented in the software package MAPMAKELR/QTL (Lincoln and Lander, 1990). Additional software includes Qgene, Version 2.23 (1996) (Department of Plant Breeding and Biometry, 266 Emerson Hall, Cornell University, Ithaca, N.Y.).

B. Inherited Markers

Genetic markers comprise detected differences (polymorphisms) in the genetic information carried by two or more plants. Genetic mapping of a locus with genetic markers typically requires two fundamental components: detectably polymorphic alleles and recombination or segregation of those alleles. In plants, the recombination measured is virtually always meiotic, and therefore, the two inherent requirements of animal gene mapping are polymorphic genetic markers and one or more plants in which those alleles are segregating.

Markers are preferably inherited in codominant fashion so that the presence of both alleles at a diploid locus is readily detectable, and they are free of environmental variation, i.e., their heritability is 1. A marker genotype typically comprises two marker alleles at each locus in a diploid organism such as soybeans. The marker allelic composition of each locus can be either homozygous or heterozygous. Homozygosity is a condition where both alleles at a locus are characterized by the same nucleotide sequence. Heterozygosity refers to different conditions of the gene at a locus.

A number of different markers types are available for use in genetic mapping. Exemplary genetic marker types for use with the invention include, but are not limited to, restriction fragment length polymorphisms (RFLPs), simple sequence length polymorphisms (SSLPs), amplified fragment length polymorphisms (AFLPs), single nucleotide polymorphisms (SNPs), and isozymes. Polymorphisms comprising as little as a single nucleotide change can be assayed in a number of ways. For example, detection can be made by electrophoretic techniques including a single strand conformational polymorphism (Orita et al., 1989), denaturing gradient gel electrophoresis (Myers et al., 1985), or cleavage fragment length polymorphisms (Life Technologies, Inc., Gathersberg, Md. 20877), but the widespread availability of DNA sequencing machines often makes it easier to just sequence amplified products directly. Once the polymorphic sequence difference is known, rapid assays can be designed for progeny testing, typically involving some version of PCR amplification of specific alleles (PASA, Sommer, et al., 1992), or PCR amplification of multiple specific alleles (PAMSA, Dutton and Sommer, 1991).

Restriction fragment length polymorphisms (RFLPs) are genetic differences detectable by DNA fragment lengths, typically revealed by agarose gel electrophoresis, after restriction endonuclease digestion of DNA. There are large numbers of restriction endonucleases available, characterized by their nucleotide cleavage sites and their source, e.g., EcoRI. RFLPs result from both single-bp polymorphisms within restriction site sequences and measurable insertions or deletions within a given restriction fragment RFLP are easy and relatively inexpensive to generate (require a cloned DNA, but no sequence) and are co-dominant. RFLPs have the disadvantage of being labor-intensive in the typing stage, although this can be alleviated to some extent by multiplexing many of the tasks and reutilization of blots. Most RFLP are biallelic and of lesser polymorphic content than microsatellites. For these reasons, the use of RFLP in animal gene maps has waned.

One of skill in the art would recognize that many types of molecular markers are useful as tools to monitor genetic inheritance and are not limited to RFLPs, SSRs and SNPs, and one of skill would also understand that a variety of detection methods may be employed to track the various molecular markers. One skilled in the art would also recognize that markers of different types may be used for mapping, especially as technology evolves and new types of markers and means for identification are identified.

For purposes of convenience, inherited marker genotypes maybe converted to numerical scores, e.g., if there are 2 forms of an SNP, or other marker, designated A and B, at a particular locus using a particular enzyme, then diploid complements may be converted to a numerical score, for example, are AA=2, AB=1, and BB=0; or AA=1, AB=0 and BB=1. The absolute values of the scores are not important. What is important is the additive nature of the numeric designations. The above scores relate to codominant markers. A similar scoring system can be given that is consistent with dominant markers.

C. Marker Assisted Selection

The invention provides soybean plants with a mid/low-linolenic acid content in combination with a commercially significant yield and agronomically elite characteristics. Such plants may be produced in accordance with the invention by marker assisted selection methods comprising assaying genomic DNA for the presence of markers that are genetically linked to a Fad3-1b and/or Fad3-1c allele conferring decreased linolenic acid.

In certain embodiments of the invention it may be desired to obtain additional markers linked to Fad3-1b and/or Fad3-1c alleles. This may be carried out, for example, by first preparing an $F_2$ population by selfing an F1 hybrid produced by crossing inbred varieties only one of which comprises a Fad3-1b and/or Fad3-1c allele conferring decreased linolenic acid content. Recombinant inbred lines (RIL) (genetically related lines; usually >$F_5$, developed from continuously selfing $F_2$ lines towards homozygosity) can then be prepared and used as a mapping population. Information obtained from dominant markers can be maximized by using RIL because all loci are homozygous or nearly so.

Backcross populations (e.g., generated from a cross between a desirable variety (recurrent parent) and another variety (donor parent) carrying a trait not present in the former can also be utilized as a mapping population. A series of backcrosses to the recurrent parent can be made to recover most of its desirable traits. Thus a population is created consisting of individuals similar to the recurrent parent but each individual carries varying amounts of genomic regions from the donor parent. Backcross populations can be useful for mapping dominant markers if all loci in the recurrent parent are homozygous and the donor and recurrent parent have contrasting polymorphic marker alleles (Reiter et al., 1992).

Useful populations for mapping purposes are near-isogenic lines (NIL). NILs are created by many backcrosses to produce an array of individuals that are nearly identical in genetic composition except for the desired trait or genomic region can be used as a mapping population. In mapping with NILs, only a portion of the polymorphic loci are expected to map to a selected region. Mapping may also be carried out on transformed plant lines.

D. Plant Breeding Methods

Breeding techniques take advantage of a plant's method of pollination. There are two general methods of pollination: self-pollination which occurs if pollen from one flower is transferred to the same or another flower of the same plant, and cross-pollination which occurs if pollen comes to it from a flower on a different plant. Plants that have been self-pollinated and selected for type over many generations become homozygous at almost all gene loci and produce a uniform population of true breeding progeny, homozygous plants.

In development of suitable varieties, pedigree breeding may be used. The pedigree breeding method for specific traits involves crossing two genotypes. Each genotype can have one or more desirable characteristics lacking in the other; or, each genotype can complement the other. If the two original parental genotypes do not provide all of the desired characteristics, other genotypes can be included in the breeding population. Superior plants that are the products of these crosses are selfed and are again advanced in each successive generation. Each succeeding generation becomes more homogeneous as a result of self-pollination and selection. Typically, this method of breeding involves five or more generations of selfing and selection: $S_1 \rightarrow S_2$; $S_2 \rightarrow S_3$; $S_3 \rightarrow S_4$; $S_4 \rightarrow S_5$, etc. A selfed generation (S) may be considered to be a type of filial generation (F) and may be named F as such. After at least five generations, the inbred plant is considered genetically pure.

Each breeding program should include a periodic, objective evaluation of the efficiency of the breeding procedure. Evaluation criteria vary depending on the goal and objectives. Promising advanced breeding lines are thoroughly tested and compared to appropriate standards in environments representative of the commercial target area(s) for generally three or more years. Identification of individuals that are genetically superior because genotypic value can be masked by confounding plant traits or environmental factors. One method of identifying a superior plant is to observe its performance relative to other experimental plants and to one or more widely grown standard varieties. Single observations can be inconclusive, while replicated observations provide a better estimate of genetic worth.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued. Descriptions of other breeding methods that are commonly used for different traits and crops can be found in one of several reference books (e.g., Allard, 1960; Simmonds, 1979; Sneep et al., 1979; Fehr, 1987a,b).

The effectiveness of selecting for genotypes with traits of interest (e.g., high yield, disease resistance, fatty acid profile) in a breeding program will depend upon: 1) the extent to which the variability in the traits of interest of individual plants in a population is the result of genetic factors and is thus transmitted to the progenies of the selected genotypes; and 2) how much the variability in the traits of interest among the plants is due to the environment in which the different genotypes are growing. The inheritance of traits ranges from control by one major gene whose expression is not influenced by the environment (i.e., qualitative characters) to control by many genes whose effects are greatly influenced by the environment (i.e., quantitative characters). Breeding for quantitative traits such as yield is further characterized by the fact that: 1) the differences resulting from the effect of each gene are small, making it difficult or impossible to identify them individually; 2) the number of genes contributing to a character is large, so that distinct segregation ratios are seldom if ever obtained; and 3) the effects of the genes may be expressed in different ways based on environmental variation. Therefore, the accurate identification of transgressive segregates or superior genotypes with the traits of interest is extremely difficult and its success is dependent on the plant breeder's ability to minimize the environmental variation affecting the expression of the quantitative character in the population.

The likelihood of identifying a transgressive segregant is greatly reduced as the number of traits combined into one genotype is increased. For example, if a cross is made between cultivars differing in three complex characters, such as yield, linolenic acid content and at least a first agronomic trait, it is extremely difficult without molecular tools to recover simultaneously by recombination the maximum number of favorable genes for each of the three characters into one genotype. Consequently, all the breeder can generally hope for is to obtain a favorable assortment of genes for the first complex character combined with a favorable assortment of genes for the second character into one genotype in addition to a selected gene.

Backcrossing is an efficient method for transferring specific desirable traits. This can be accomplished, for example, by first crossing a superior variety inbred (A) (recurrent parent) to a donor inbred (non-recurrent parent), which carries the appropriate gene(s) for the trait in question (Fehr, 1987). The progeny of this cross are then mated back to the superior recurrent parent (A) followed by selection in the resultant progeny for the desired trait to be transferred from the non-recurrent parent. Such selection can be based on genetic assays, as mentioned below, or alternatively, can be based on the phenotype of the progeny plant. After five or more backcross generations with selection for the desired trait, the progeny are heterozygous for loci controlling the characteristic being transferred, but are like the superior parent for most or almost all other genes. The last generation of the backcross is selfed, or sibbed, to give pure breeding progeny for the gene(s) being transferred, for example, loci providing the plant with decreased linolenic acid content.

In one embodiment of the invention, the process of backcross conversion may be defined as a process including the steps of:
(a) crossing a plant of a first genotype containing one or more desired gene, DNA sequence or element, such as Fad3-1b and/or Fad3-1c alleles associated with decreased linolenic acid content, to a plant of a second genotype lacking said desired gene, DNA sequence or element;
(b) selecting one or more progeny plant containing the desired gene, DNA sequence or element;
(c) crossing the progeny plant to a plant of the second genotype; and
(d) repeating steps (b) and (c) for the purpose of transferring said desired gene, DNA sequence or element from a plant of a first genotype to a plant of a second genotype.

Introgression of a particular DNA element or set of elements into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid. During breeding, the genetic markers linked to decreased linolenic acid content may be used to assist in breeding for the purpose of producing soybean plants with decreased linolenic acid content and preferably a mid/low-linolenic acid content. Backcrossing and marker assisted selection in particular can be used with the present invention to introduce the decreased linolenic acid content trait in accordance with the current invention into any variety by conversion of that variety with Fad3-1b and/or Fad3-1c alleles associated with the trait, with both loci being preferred.

The selection of a suitable recurrent parent is an important step for a successful backcrossing procedure. The goal of a backcross protocol is to alter or substitute a trait or characteristic in the original inbred. To accomplish this, one or more loci of the recurrent inbred is modified or substituted with the desired gene from the nonrecurrent parent, while retaining essentially all of the rest of the desired genetic, and therefore the desired physiological and morphological, constitution of the original inbred. The choice of the particular nonrecurrent parent will depend on the purpose of the backcross, which in the case of the present invention may be add one or more allele conferring decreased linolenic acid content. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred. In the case of the present invention, one may test the linolenic acid content of progeny lines generated during the backcrossing program as well as using the marker system described herein to select lines based upon markers rather than visual traits.

Soybean plants (*Glycine max* L.) can be crossed by either natural or mechanical techniques (see, e.g., Fehr, 1980). Natural pollination occurs in soybeans either by self pollination or natural cross pollination, which typically is aided by pollinating organisms. In either natural or artificial crosses, flowering and flowering time are an important consideration. Soybean is a short-day plant, but there is considerable genetic variation for sensitivity to photoperiod (Hamner, 1969; Criswell and Hume, 1972). The critical day length for flowering ranges from about 13 h for genotypes adapted to tropical latitudes to 24 h for photoperiod-insensitive genotypes grown at higher latitudes (Shibles et al., 1975). Soybeans seem to be insensitive to day length for 9 days after emergence. Photoperiods shorter than the critical day length are required for 7 to 26 days to complete flower induction (Borthwick and Parker, 1938; Shanmugasundaram and Tsou, 1978).

Soybean flowers typically are self-pollinated on the day the corolla opens. The stigma is receptive to pollen about 1 day before anthesis and remains receptive for 2 days after anthesis, if the flower petals are not removed. Filaments of nine stamens are fused, and the one nearest the standard is free. The stamens form a ring below the stigma until about 1 day before anthesis, then their filaments begin to elongate rapidly and elevate the anthers around the stigma. The anthers dehisce on the day of anthesis, pollen grains fall on the stigma, and within 10 h the pollen tubes reach the ovary and fertilization is completed (Johnson and Bernard, 1963). Self-pollination occurs naturally in soybean with no manipulation of the flowers. For the crossing of two soybean plants, it is typically preferable, although not required, to utilize artificial hybridization. In artificial hybridization, the flower used as a female in a cross is manually cross pollinated prior to maturation of pollen from the flower, thereby preventing self fertilization, or alternatively, the male parts of the flower are emasculated using a technique known in the art. Techniques for emasculating the male parts of a soybean flower include, for example, physical removal of the male parts, use of a genetic factor conferring male sterility, and application of a chemical gametocide to the male parts.

Either with or without emasculation of the female flower, hand pollination can be carried out by removing the stamens and pistil with a forceps from a flower of the male parent and gently brushing the anthers against the stigma of the female flower. Access to the stamens can be achieved by removing the front sepal and keel petals, or piercing the keel with closed forceps and allowing them to open to push the petals away. Brushing the anthers on the stigma causes them to rupture, and the highest percentage of successful crosses is obtained when pollen is clearly visible on the stigma. Pollen shed can be checked by tapping the anthers before brushing the stigma. Several male flowers may have to be used to obtain suitable pollen shed when conditions are unfavorable, or the same male may be used to pollinate several flowers with good pollen shed.

Genetic male sterility is available in soybeans and may be useful to facilitate hybridization in the context of the current invention, particularly for recurrent selection programs (Brim and Stuber, 1973). The distance required for complete isolation of a crossing block is not clear; however, outcrossing is less than 0.5% when male-sterile plants are 12 m or more from a foreign pollen source (Boerma and Moradshahi, 1975). Plants on the boundaries of a crossing block probably sustain the most outcrossing with foreign pollen and can be eliminated at harvest to minimize contamination.

Once harvested, pods are typically air-dried at not more than 38° C. until the seeds contain 13% moisture or less, then the seeds are removed by hand. Seed can be stored satisfactorily at about 25° C. for up to a year if relative humidity is 50% or less. In humid climates, germination percentage declines rapidly unless the seed is dried to 7% moisture and stored in an air-tight container at room temperature. Long-term storage in any climate is best accomplished by drying seed to 7% moisture and storing it at 10° C. or less in a room maintained at 50% relative humidity or in an air-tight container.

III. TRAITS FOR MODIFICATION AND IMPROVEMENT OF SOYBEAN VARIETIES

In certain embodiments, a soybean plant provided by the invention may comprise one or more transgene(s). One example of such a transgene confers herbicide resistance. Common herbicide resistance genes include an EPSPS gene conferring glyphosate resistance, a neomycin phosphotransferase II (nptII) gene conferring resistance to kanamycin (Fraley et al., 1983), a hygromycin phosphotransferase gene conferring resistance to the antibiotic hygromycin (Vanden Elzen et al., 1985), genes conferring resistance to glufosinate or broxynil (Comai et al., 1985; Gordon-Kamm et al., 1990; Stalker et al., 1988) such as dihydrofolate reductase and acetolactate synthase (Eichholtz et al., 1987, Shah et al., 1986, Charest et al., 1990). Further examples include mutant ALS and AHAS enzymes conferring resistance to imidazalinone or a sulfonylurea (Lee et al., 1988; Miki et al., 1990), a phosphinothricin-acetyl-transferase gene conferring phosphinothricin resistance (European Appln. 0 242 246), genes conferring resistance to phenoxy proprionic acids and cycloshexones, such as sethoxydim and haloxyfop (Marshall et al., 1992); and genes conferring resistance to triazine (psbA and gs+ genes) and benzonitrile (nitrilase gene) (Przibila et al., 1991).

A plant of the invention may also comprise a gene that confers resistance to insect, pest, viral or bacterial attack. For example, a gene conferring resistance to a pest, such as soybean cyst nematode was described in PCT Application WO96/30517 and PCT Application WO93/19181. Jones et al., (1994) describe cloning of the tomato Cf-9 gene for resistance to *Cladosporium fulvum*); Martin et al., (1993) describe a tomato Pto gene for resistance to *Pseudomonas syringae* pv. and Mindrinos et al., (1994) describe an *Arabidopsis* RSP2 gene for resistance to *Pseudomonas syringae*. *Bacillus thuringiensis* endotoxins may also be used for insect resistance. (See, for example, Geiser et al., (1986). A vitamin-binding protein such as avidin may also be used as a larvicide (PCT application US93/06487).

The use of use of viral coat proteins in transformed plant cells is known to impart resistance to viral infection and/or disease development affected by the virus from which the coat protein gene is derived, as well as by related viruses. (See Beachy et al., 1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id. Developmental-arrestive proteins produced in nature by a pathogen or a parasite may also be used. For example, Logemann et al., (1992), have shown that transgenic plants expressing the barley ribosome-inactivating gene have an increased resistance to fungal disease.

Transgenes may also be used conferring increased nutritional value or another value-added trait. One example is modified fatty acid metabolism, for example, by transforming a plant with an antisense gene of stearoyl-ACP desaturase to increase stearic acid content of the plant. (See Knutzon et al., 1992). A sense desaturase gene may also be introduced to alter fatty acid content. Phytate content may be modified by introduction of a phytase-encoding gene to enhance breakdown of phytate, adding more free phosphate to the transformed plant. Modified carbohydrate composition may also be affected, for example, by transforming plants with a gene coding for an enzyme that alters the branching pattern of starch. (See Shiroza et al., 1988) (nucleotide sequence of *Streptococcus* mutants fructosyltransferase gene); Steinmetz et al., (1985) (nucleotide sequence of *Bacillus subtilis* levansucrase gene); Pen et al., (1992) (production of transgenic plants that express *Bacillus lichenifonnis* α-amylase); Elliot et al., (1993) (nucleotide sequences of tomato invertase genes); Søgaard et al., (1993) (site-directed mutagenesis of barley α-amylase gene); and Fisher et al., (1993) (maize endosperm starch branching enzyme II)).

Transgenes may also be used to alter protein metabolism. For example, U.S. Pat. No. 5,545,545 describes lysine-insensitive maize dihydrodipicolinic acid synthase (DHPS), which is substantially resistant to concentrations of L-lysine which otherwise inhibit the activity of native DHPS. Similarly, EP 0640141 describes sequences encoding lysine-insensitive aspartokinase (AK) capable of causing a higher than normal production of threonine, as well as a subfragment encoding antisense lysine ketoglutarate reductase for increasing lysine.

In another embodiment, a transgene may be employed that alters plant carbohydrate metabolism. For example, fructokinase genes are known for use in metabolic engineering of fructokinase gene expression in transgenic plants and their fruit (see U.S. Pat. No. 6,031,154). A further example of transgenes that may be used are genes that alter grain yield. For example, U.S. Pat. No. 6,486,383 describes modification of starch content in plants with subunit proteins of adenosine diphosphoglucose pyrophosphorylase ("ADPG PPase"). In EP0797673, transgenic plants are discussed in which the introduction and expression of particular DNA molecules results in the formation of easily mobilised phosphate pools outside the vacuole and an enhanced biomass production and/or altered flowering behavior. Still further known are genes for altering plant maturity. U.S. Pat. No. 6,774,284 describes DNA encoding a plant lipase and methods of use thereof for controlling senescence in plants. U.S. Pat. No. 6,140,085 discusses FCA genes for altering flowering characteristics, particularly timing of flowering. U.S. Pat. No. 5,637,785 discusses genetically modified plants having modulated flower development such as having early floral meristem development and comprising a structural gene encoding the LEAFY protein in its genome.

Genes for altering plant morphological characteristics are also known and may be used in accordance with the invention. U.S. Pat. No. 6,184,440 discusses genetically engineered plants which display altered structure or morphology as a result of expressing a cell wall modulation transgene. Examples of cell wall modulation transgenes include a cellulose binding domain, a cellulose binding protein, or a cell wall modifying protein or enzyme such as endoxyloglucan transferase, xyloglucan endo-transglycosylase, an expansin, cellulose synthase, or a novel isolated endo-1,4-β-glucanase.

Methods for introduction of a transgene are well known in the art and include biological and physical, plant transformation protocols. See, for example, Miki et al (1993).

Once a transgene is introduced into a variety it may readily be transferred by crossing. By using backcrossing, essentially all of the desired morphological and physiological characteristics of a variety are recovered in addition to the locus transferred into the variety via the backcrossing technique. Backcrossing methods can be used with the present invention to improve or introduce a characteristic into a plant (Poehlman et al., 1995; Fehr, 1987a,b).

IV. TISSUE CULTURES AND IN VITRO REGENERATION OF SOYBEAN PLANTS

A further aspect of the invention relates to tissue cultures of a soybean variety of the invention. As used herein, the term "tissue culture" indicates a composition comprising isolated cells of the same or a different type or a collection of such cells organized into parts of a plant. Exemplary types of tissue cultures are protoplasts, calli and plant cells that are intact in plants or parts of plants, such as embryos, pollen, flowers, leaves, roots, root tips, anthers, and the like. In a preferred embodiment, the tissue culture comprises embryos, protoplasts, meristematic cells, pollen, leaves or anthers.

Exemplary procedures for preparing tissue cultures of regenerable soybean cells and regenerating soybean plants therefrom, are disclosed in U.S. Pat. No. 4,992,375; U.S. Pat. No. 5,015,580; U.S. Pat. No. 5,024,944, and U.S. Pat. No. 5,416,011, each of the disclosures of which is specifically incorporated herein by reference in its entirety.

An important ability of a tissue culture is the capability to regenerate fertile plants. This allows, for example, transformation of the tissue culture cells followed by regeneration of transgenic plants. For transformation to be efficient and successful, DNA must be introduced into cells that give rise to plants or germ-line tissue.

Soybeans typically are regenerated via two distinct processes; shoot morphogenesis and somatic embryogenesis (Finer, 1996). Shoot morphogenesis is the process of shoot meristem organization and development. Shoots grow out from a source tissue and are excised and rooted to obtain an intact plant. During somatic embryogenesis, an embryo (similar to the zygotic embryo), containing both shoot and root axes, is formed from somatic plant tissue. An intact plant rather than a rooted shoot results from the germination of the somatic embryo.

Shoot morphogenesis and somatic embryogenesis are different processes and the specific route of regeneration is primarily dependent on the explant source and media used for tissue culture manipulations. While the systems are different, both systems show variety-specific responses where some lines are more responsive to tissue culture manipulations than others. A line that is highly responsive in shoot morphogenesis may not generate many somatic embryos. Lines that produce large numbers of embryos during an 'induction' step may not give rise to rapidly-growing proliferative cultures. Therefore, it may be desired to optimize tissue culture conditions for each soybean line. These optimizations may readily be carried out by one of skill in the art of tissue culture through small-scale culture studies. In addition to line-specific responses, proliferative cultures can be observed with both shoot morphogenesis and somatic embryogenesis. Proliferation is beneficial for both systems, as it allows a single, transformed cell to multiply to the point that it will contribute to germ-line tissue.

Shoot morphogenesis was first reported by Wright et al. (1986) as a system whereby shoots were obtained de novo from cotyledonary nodes of soybean seedlings. The shoot meristems were formed subepidermally and morphogenic tissue could proliferate on a medium containing benzyl adenine (BA). This system can be used for transformation if the subepidermal, multicellular origin of the shoots is recognized and proliferative cultures are utilized. The idea is to target tissue that will give rise to new shoots and proliferate those cells within the meristematic tissue to lessen problems associated with chimerism. Formation of chimeras, resulting from transformation of only a single cell in a meristem, are problematic if the transformed cell is not adequately proliferated and does not does not give rise to germ-line tissue. Once the system is well understood and reproduced satisfactorily, it can be used as one target tissue for soybean transformation.

Somatic embryogenesis in soybean was first reported by Christianson et al. (1983) as a system in which embryogenic tissue was initially obtained from the zygotic embryo axis. These embryogenic cultures were proliferative but the repeatability of the system was low and the origin of the embryos was not reported. Later histological studies of a different proliferative embryogenic soybean culture showed that proliferative embryos were of apical or surface origin with a small number of cells contributing to embryo formation. The origin of primary embryos (the first embryos derived from the initial explant) is dependent on the explant tissue and the auxin levels in the induction medium (Hartweck et al., 1988). With proliferative embryonic cultures, single cells or small groups of surface cells of the 'older' somatic embryos form the 'newer' embryos.

Embryogenic cultures can also be used successfully for regeneration, including regeneration of transgenic plants, if the origin of the embryos is recognized and the biological limitations of proliferative embryogenic cultures are understood. Biological limitations include the difficulty in developing proliferative embryogenic cultures and reduced fertility problems (culture-induced variation) associated with plants regenerated from long-term proliferative embryogenic cultures. Some of these problems are accentuated in prolonged cultures. The use of more recently cultured cells may decrease or eliminate such problems.

V. UTILIZATION OF SOYBEAN PLANTS

A soybean plant provided by the invention may be used for any purpose deemed of value. Common uses include the preparation of food for human consumption, feed for non-human animal consumption and industrial uses. As used herein, "industrial use" or "industrial usage" refers to non-food and non-feed uses for soybeans or soy-based products.

Soybeans are commonly processed into two primary products, soybean protein (meal) and crude soybean oil. Both of these products are commonly further refined for particular uses. Refined oil products can be broken down into glycerol, fatty acids and sterols. These can be for food, feed or industrial usage. Edible food product use examples include coffee creamers, margarine, mayonnaise, pharmaceuticals, salad dressings, shortenings, bakery products, and chocolate coatings.

Soy protein products (e.g., meal), can be divided into soy flour concentrates and isolates which have both food/feed and industrial use. Soy flour and grits are often used in the manufacturing of meat extenders and analogs, pet foods, baking ingredients and other food products. Food products made from soy flour and isolate include baby food, candy products, cereals, food drinks, noodles, yeast, beer, ale, etc. Soybean meal in particular is commonly used as a source of protein in livestock feeding, primarily swine and poultry. Feed uses thus include, but are not limited to, aquaculture feeds, bee feeds, calf feed replacers, fish feed, livestock feeds, poultry feeds and pet feeds, etc.

Whole soybean products can also be used as food or feed. Common food usage includes products such as the seed, bean sprouts, baked soybean, full fat soy flour used in various products of baking, roasted soybean used as confectioneries, soy nut butter, soy coffee, and other soy derivatives of oriental foods. For feed usage, hulls are commonly removed from the soybean and used as feed.

Soybeans additionally have many industrial uses. One common industrial usage for soybeans is the preparation of binders that can be used to manufacture composites. For example, wood composites may be produced using modified soy protein, a mixture of hydrolyzed soy protein and PF resins, soy flour containing powder resins, and soy protein containing foamed glues. Soy-based binders have been used to manufacture common wood products such as plywood for over 70 years. Although the introduction of urea-formaldehyde and phenol-formaldehyde resins has decreased the usage of soy-based adhesives in wood products, environmental concerns and consumer preferences for adhesives made from a renewable feedstock have caused a resurgence of interest in developing new soy-based products for the wood composite industry.

Preparation of Adhesives Represents Another Common Industrial Usage for Soybeans. Examples of soy adhesives include soy hydrolyzate adhesives and soy flour adhesives. Soy hydrolyzate is a colorless, aqueous solution made by reacting soy protein isolate in a 5 percent sodium hydroxide solution under heat (120° C.) and pressure (30 psig). The resulting degraded soy protein solution is basic (pH 11) and flowable (approximately 500 cps) at room temperature. Soy flour is a finely ground, defatted meal made from soybeans. Various adhesive formulations can be made from soy flour, with the first step commonly requiring dissolving the flour in a sodium hydroxide solution. The strength and other properties of the resulting formulation will vary depending on the additives in the formulation. Soy flour adhesives may also potentially be combined with other commercially available resins.

Soybean oil may find application in a number of industrial uses. Soybean oil is the most readily available and one of the lowest-cost vegetable oils in the world. Common industrial uses for soybean oil include use as components of anti-static agents, caulking compounds, disinfectants, fungicides, inks, paints, protective coatings, wallboard, anti-foam agents, alcohol, margarine, paint, ink, rubber, shortening, cosmetics, etc. Soybean oils have also for many years been a major ingredient in alkyd resins, which are dissolved in carrier solvents to make oil-based paints. The basic chemistry for converting vegetable oils into an alkyd resin under heat and pressure is well understood to those of skill in the art.

Soybean oil in its commercially available unrefined or refined, edible-grade state, is a fairly stable and slow-drying oil. Soybean oil can also be modified to enhance its reactivity under ambient conditions or, with the input of energy in various forms, to cause the oil to copolymerize or cure to a dry film. Some of these forms of modification have included epoxidation, alcoholysis or tranesterification, direct esterification, metathesis, isomerization, monomer modification, and various forms of polymerization, including heat bodying. The reactive linoleic-acid component of soybean oil with its double bonds may be more useful than the predominant oleic- and linoleic-acid components for many industrial uses.

Solvents can also be prepared using soy-based ingredients. For example, methyl soyate, a soybean-oil based methyl ester, is gaining market acceptance as an excellent solvent replacement alternative in applications such as parts cleaning and degreasing, paint and ink removal, and oil spill remediation. It is also being marketed in numerous formulated consumer products including hand cleaners, car waxes and graffiti removers. Methyl soyate is produced by the transesterification of soybean oil with methanol. It is commercially available from numerous manufacturers and suppliers. As a solvent, methyl soyate has important environmental- and safety-related properties that make it attractive for industrial applications. It is lower in toxicity than most other solvents, is readily biodegradable, and has a very high flash point and a low level of volatile organic compounds (VOCs). The compatibility of methyl soyate is excellent with metals, plastics, most elastomers and other organic solvents. Current uses of methyl soyate include cleaners, paint strippers, oil spill cleanup and bioremediation, pesticide adjuvants, corrosion preventives and biodiesel fuels additives.

VI. DEFINITIONS

In the description and tables which follow, a number of terms are used. In order to provide a clear and consistent understanding of the specification and claims, the following definitions are provided:

A: When used in conjunction with the word "comprising" or other open language in the claims, the words "a" and "an" denote "one or more."

Agronomically Elite As used herein, means a genotype that has a culmination of many distinguishable traits such as emergence, vigor, vegetative vigor, disease resistance, seed set, standability and threshability which allows a producer to harvest a product of commercial significance.

Allele: Any of one or more alternative forms of a gene locus, all of which alleles relate to a trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Commercially Significant Yield: A yield of grain having commercial significance to the grower represented by an actual grain yield of 103% of the check lines AG2703 and DKB23-51 when grown under the same conditions.

Crossing: The mating of two parent plants.

Cross-pollination: Fertilization by the union of two gametes from different plants.

$F_1$ Hybrid: The first generation progeny of the cross of two nonisogenic plants.

Genotype: The genetic constitution of a cell or organism.

Industrial use: A non-food and non-feed use for a soybean plant. The term "soybean plant" includes plant parts and derivatives of a soybean plant.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Stringent Conditions: Refers to nucleic acid hybridization conditions of 5×SSC, 50% formamide and 42° C.

Substantially Equivalent: A characteristic that, when compared, does not show a statistically significant difference (e.g., p=0.05) from the mean.

Tissue Culture: A composition comprising isolated cells of the same or a different type or a collection of such cells organized into parts of a plant.

Transgene: A genetic locus comprising a sequence which has been introduced into the genome of a soybean plant by transformation.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Mapping Populations and Identification of Polymorphisms

Low linolenic lines 6P248, T27111, T27190, T26767 and T26830 were selected for use in identifying low-lin associated polymorphisms in maturity groups 1-4. The linolenic acid content of these lines was around 3%. The low-lin lines Soyola and N98-44 will be used in maturity groups 4-5. Other low-lin lines include A5 and C1640. Sixteen wild type lines with the following commercial designations were also used: A2247, AG1902, AG2402, AG2703, AG3201, AG3302, AG3702, AJB2102J0C, AJB2302K0C, CSR2533, CSR2622N, CSR3922N, DKB19-51, DKB23-95 and WP25920. To facilitate mapping efforts, lines from previously used mapping populations, HS-1 and P1507354(PIC), were used in some sequencing regions. DNA was isolated from each genotype using standard DNA extraction protocols.

Nested primers were designed to completely cover the loci Fad3-1a, Fad3-1b, and Fad3-1c. The amplicons generated were from different lines. Sequences of these amplicons were aligned to identify SNPs and Indels associated with the low linolenic phenotypes. Initially, 13 pairs of primers were designed from Fad3-1a, 6 pairs from Fad3-1b, and 12 pairs from Fad3-1c. An additional 14 pairs of primers were designed for Fad3-1c from introns once their sequences were determined from this study. Table 1 lists the primers used in this analysis. Sequence alignment was done with Seqman program of DNA Star package.

Taqman assays were designed and manufactured by Applied Biosystems based on the SNP sequences. SNP detection was done according to the instruction of Applied Biosystems.

TABLE 1

Primers Designed for Resequencing on
Fad3-1a, Fad3-1b and Fad3-1c genes
(SEQ ID NOs:4-82, respectively)

| | |
|---|---|
| FAD3_1A1F | CCTATTCTAGGTTTTTACGCACCA |
| FAD3_1A1R | AAGTTGTCTAAAGCCAAATGAAGAA |
| FAD3_1A2F | GGACATGATTGGTAATAATTTTTGTG |
| FAD3_1A2R | AGGAAGCATAAAGATTCCCTTTTT |
| FAD3_1A3F | AAAGGGAATCTTTATGCTTCCTG |
| FAD3_1A3R | TCTGCACATGATCAAACAATTACA |
| FAD3_1A4F | ATGTAATTGTTTGATCATGTGCAG |
| FAD3_1A4R | AAAATAAAATCTTGTGGGTGCAAT |
| FAD3_1A5F | TGGCGGATCTATGTAAATGAGTG |
| FAD3_1A5R | AATGAAAAACGGGGCTTGTAA |
| FAD3_1A6F | TTTTGTTGGTCAAGGGACTTAGAT |
| FAD3_1A6R | CACCACCAAGCTCCCAGTATAGTA |
| FAD3_1A7F | CCTCCTTTCTAGGTGTACATGCTT |
| FAD3_1A7R | ATCATGGATCCCATGTCTCTCTAT |
| FAD3_1A8F | TTGTTCTTGGACATGATTGGTAAT |
| FAD3_1A8R | TTCAATGACAAATGAACAAACAAA |
| FAD3_1A9F | GAAATCACATCTGGAATGTGAAAG |
| FAD3_1A9R | AATAATGTGTTGTTGTCTTCCAAGT |
| FAD3_1A10F | GAAATCACATCTGGAATGTGAAAG |
| FAD3_1A10R | GTTCAAGAACAGCCTCAGGAAG |
| FAD3_1A11F | GGTGAACACTTAAATGCGAGATAG |
| FAD3_1A11R | TTATGGGGGCAAAGTTTTATTTTA |
| FAD3_1A12F | TCCATAAATAAGTAAAACAAGTGACAA |
| FAD3_1A12R | CCACTTACCACACTTTCTTTGTTG |
| FAD3_1A13F | TCATTTTCAGTTGCATGATTCTAA |
| FAD3_1A13R | CAGAAGTATCAAAGCATGTACACC |
| FAD3_1B1F | CAACATGTTGGTAATGGTGCAGGGA |
| FAD3_1B1R | CGAACAATCATGCATAACCAA |
| FAD3_1B2F | TGCATGATTGTTCGTTCATATGTT |
| FAD3_1B2R | TGACATAAAGGCATAAAGACACAT |
| FAD3_1B3F | GATGTGAATTTCATGAAGTGGTTC |

TABLE 1-continued

Primers Designed for Resequencing on Fad3-1a, Fad3-1b and Fad3-1c genes (SEQ ID NOs:4-82, respectively)

| | |
|---|---|
| FAD3_1B3R | GGACTTGGACATGTGTTAACCTC |
| FAD3_1B4F | TATTTGCAACCTACACCGAAGTAA |
| FAD3_1B4R | ACATGGAGTAAGTTTCTACCTTCTTT |
| FAD3_1B5F | TATTTGCAACCTACACCGAAGTAA |
| FAD3_1B5R | ACATGGAGTAAGTTTCTACCTTCTTT |
| FAD3_1B6F | TTTCTCCTATTCTACAATCAATAATCC |
| FAD3_1B6R | AAAGTAAGTGCATTTCTAGCATAATTT |
| FAD3_1C1F | AAGATTTCATTCTTCCTCTTCTAGG |
| FAD3_1C1R | AATTGAGGAATGCAAGATGTGTC |
| FAD3_1C2F | ACACATCTTGCATTCCTCAATTCT |
| FAD3_1C2R | CTTTCTGGCTCACGGTAATACTCT |
| FAD3_1C3F | TTCTTGGAGAGTATTACCGTGAGC |
| FAD3_1C3R | CAATATTTATTAATTACCACCTTAC |
| FAD3_1C4F | CTAGGTTATTACGCACCACCCA |
| FAD3_1C4R | GGAGGAGCACTGGGATCAAAAGCT |
| FAD3_1C5F | CACACTAAGCCAAAGCCAAAGCAGCAAT |
| FAD3_1C5R | AGCACTGGGATCAAAAGCTTCCTT |
| FAD3_1C6F | AATAATGGATACCAAAAGGAAGC |
| FAD3_1C6R | GTTGAAGTGACTTGCAGCAGCCAT |
| FAD3_1C7F | ATGGATACCAAAAGGAAGCTTTTG |
| FAD3_1C7R | GATAGATAAGCATAGAAAACATGGTAA |
| FAD3_1C8F | ACTGTGTTGGGTTACCATGTTTTCTA |
| FAD3_1C8R | CAATAAATAACCCAAAAATTGAAA |
| FAD3_1C9F | GCAATATCAACACTGTGTTGGGT |
| FAD3_1C9R | CTAGAATCCAATAAATAACCCAAAAAT |
| FAD3_1C10F | GAGTTTCAATTTTTGGGTTATTTA |
| FAD3_1C10R | CCATTGAGGCCCACTATGAATTCC |
| FAD3_1C11F | GAGTTTCAATTTTTGGGTT |
| FAD3_1C11R | TCCATTGAGGCCCACTATGAATTCCT |
| FAD3_1C12F | GACAGGAATTCATAGTGGGCCTCAA |
| FAD3_1C12R | CTGACAATTCAATATTTATTAATTACC |
| FAD3_1C13F | ATACTTCAGATAAAGCTGTTCTTGAA |
| FAD3_1C13R | TTGTGATACTAGTTAAGACCCATAAAA |
| FAD3_1C14F | GATAAAGCTGTTCTTGAACATTT |
| FAD3_1C14R | TTTTTGTGATACTAGTTAAGACCCATA |
| FAD3_1C15F | TTTGTCATTATCTTAGTTAACC |
| FAD3_1C15R | AAAAAGAGGAAAAAGTAATGTAAGAGT |
| FAD3_1C16F | CATTAATTATGTAATTGTTTGAACACG |
| FAD3_1C16R1 | AAACCACATCTCCAGTGTCACTTA |
| FAD3_1C16R2 | TCACTTACGAAGTGGTCTTGTCTC |
| FAD3_1C17F | TTTGAATATTTCAATTCTCCAATTA |
| FAD3_1C17R | GTTATTGATCCAACCATAGTCACG |
| FAD3_1C18F | CATTAATTATGTAATTGTTTGAACACG |
| FAD3_1C18R | GAGGTGATAATGAGGAATTTGAGG |
| FAD3_1C19F | TATTTGTTATGTGGCTGGACTTTG |
| FAD3_1C19R | AAACCACATCTCCAGTGTCACTTA |
| FAD3_1C20F | ACTTTGTCACATACTTGCATCACC |
| FAD3_1C20R | TCACTTACGAAGTGGTCTTGTCTC |

Example 2

Identification of Polymorphisms at Fad3-1a

The sequence coverage of this locus was good. Table 2 shows the polymorphism identified at this locus. Ten SNPs and three indels were detected. However, no SNP or other marker haplotype was found to be associated with the low-linolenic phenotype. Overall, sequence variation at this locus was found to be significantly higher than that at Fad3-1b and Fad3-1c, indicating that it was not under selection pressure for this trait.

TABLE 2

Polymorphisms at the Fad3-1a locus
Sequence Position

| Lines | 552 | 841 | 1495 | 2034-2042 | 2406 | 2459 | 2482-2484 | 2493 | 2963 | 3400 | 3405 | 3450 | 3557 |
|---|---|---|---|---|---|---|---|---|---|---|---|---|---|
| Original seq | G | C | T | — | G | C | ATT | — | T | A | A | A | T |
| 6P248 | G | C(2) | T(3) | — | A | C | ATT | — | T | A | A | A | T |
| T27111 | G | T | C | + | G | C | ATT | T | T | | | G | G |
| T27190 | G | C | T | — | G | C | ATT | — | T | | | A | T |
| T26767 | G | T | C | + | G | T | ATT | T | T | A | A | G | G |
| T26830 | | C | | — | | | | — | | A | A | A | |
| A5 | T(2) | T | T | + | A | C | ATT | — | G | A | A | G | T |
| C1640 | G | T | C | — | G | T | ATT | T | T | A/T | A/T | G | G |
| Soyola | T | T | C | + | A | C | ATT | — | G | T | T | G | T |
| N98-4445 | G | T | T | + | A | C | ATT | — | G | T | T | A/G | T |

TABLE 2-continued

Polymorphisms at the Fad3-1a locus
Sequence Position

| Lines | 552 | 841 | 1495 | 2034-2042 | 2406 | 2459 | 2482-2484 | 2493 | 2963 | 3400 | 3405 | 3450 | 3557 |
|---|---|---|---|---|---|---|---|---|---|---|---|---|---|
| A2247 | G | C | T(2) | − | G | | ATT | — | T | A/T | T/A | A | T |
| AG1701 | G | T | C | + | G | C | ATT | T | T | T | T | | G |
| AG1902 | T | T | C | + | A | C | ATT | — | T | A/T | T/A | G | T |
| AG2402 | G | T | C | + | G | T | — | — | T | T/A | T/A | A | T |
| AG2703 | G | T | T | − | G | C | ATT | — | G | T/A | T/A | A | T |
| AG3201 | T | T | C | + | A | C | ATT | — | G | T | T | G | T |
| AG3302 | G | T | C | + | G | T | ATT | T | G | T/A | T/A | G | G |
| AG3702 | T | T | C | + | A | C | ATT | — | G | | | A/G | T |
| AJB2102J0C | G | C | T(3) | − | G | C | ATT | — | T | T | T | A | T |
| AJB2302K0C | G | C | T(3) | − | G | C | ATT | — | T | A/T | T/A | A | T |
| CSR2533 | G | T | C | + | G | T | ATT | T | T | T/A | T/A | G | G |
| CSR2622N | G | T | C | + | G | T | ATT | T | T | | | | |
| CSR3922N | G | C | T(3) | − | G | C | ATT | — | T | T/A | T/A | A | T |
| DKB19-51 | G | T | C | + | G | T | ATT | — | T | | | | |
| DKB23-95 | T | T | C | + | A | C | ATT | — | G | T | T | A/G | |
| WP25920 | G | T | T(2) | + | G | C | ATT | — | T | | | A | T |

Note:
The number in the parenthesis indicates number of sequence reads in a given line Example 3

Identification of Polymorphisms at Fad3-1b

The intron sequences of Fad3-1b were quite different from Fad3-1a, which allowed the efficient generation of locus specific amplicons. The quality of sequences from most of the lines was generally high except for a small portion of the 5'UTR region. A single nucleotide polymorphism at position 2021 was detected among all the lines in an entire sequence length of 2683 bp (Table 3). Interestingly, the SNP was found to associate with a low-lin phenotype. Low-linolenic lines 6P248, T27111, T27190, T26767 and T26830 were found to carry a "C" allele at this position while all other lines carried a "T". The five lines with a "C" allele were tested for linolenic acid content and all found to have less than 4% linolenic acid. Other low-lin lines such as A5, Soyola, and N98-4445 carried a wild type allele at this locus, indicating that one or more other loci contribute to the low-lin phenotype in these lines.

To determine whether the SNP at 2021 position was a sense mutation, the ORF was translated into protein. This showed that the mutation in the low linolenic line changed an amino acid residue from Histidine to Tyrosine. The histidine residue has been found to be critical in a number of genes involved with desaturation. The SNP found caused a mutation in the motif His-Val-Ile-His-His to His-Val-Ile-His-Tyr in the low linolenic lines. The motif has been associated with a low-lin phenotype and is a likely cause for the reduced linolenic acid.

TABLE 3

Polymorphism at the Fad3-1b locus

| Lines | Posi 2021 |
|---|---|
| Orig seq | C |
| 6P248 | T(4) |
| T27111 | T(2) |
| T27190 | T(3) |
| T26767 | T(2) |
| T26830 | T(2) |
| A5 | C(3) |
| C1640 | C(3) |
| Soyola | C(4) |
| N98-4445 | C(2) |
| A2247 | C(3) |

TABLE 3-continued

Polymorphism at the Fad3-1b locus

| Lines | Posi 2021 |
|---|---|
| AG1701 | C(2) |
| AG1902 | C(2) |
| AG2402 | C(2) |
| AG2703 | C(2) |
| AG3201 | C(2) |
| AG3302 | C(2) |
| AG3702 | C(2) |
| AJB2102J0C | C(2) |
| AJB2302K0C | C(2) |
| CSR2533 | C(2) |
| CSR2622N | C(2) |
| CSR3922N | C(2) |
| DKB19-51 | C(2) |
| DKB23-95 | C(3) |
| WP25920 | C(2) |

Note:
The number in the parenthesis indicates number of sequence reads in a given line Example 4

Identification of Polymorphisms at Fad3-1c

No genomic DNA was initially available for Fad3-1c. However, cDNA was highly conserved between Fad3-1a and Fad3-1c across the entire gene with a sequence identity of higher than 90%. To amplify introns using primers from exons, a number of primers targeting Fad3-1c specific regions were manually picked. Once the new sequences were known, new primers were designed from introns. Using this approach, partial sequences were successfully obtained covering all of the introns. Sequence analysis indicated that the Fad3-1c allele was very similar to the Fad3-1a locus even in the introns. A very high sequence similarity was observed near exon/intron junctions between the two loci, but decreased as sequences extended further.

From the sequences obtained, four SNPs and one indel were identified at Fad3-1c (Table 4). The SNPs at positions 687, 2316, 3743, as well as the indel at 1129, appeared to be in linkage equilibrium and associated with the low-linolenic phenotype. Low-linolenic lines, Soyola and N98-4445 both carried a different allele at positions 687 and 1129 from all the other lines. Although sequences were not obtained from all the lines at positions 3360 and 3743, it was indicated that these loci are in linkage equilibrium with 687 and 1129. All four positive SNPs/Indel were located in introns.

It was interesting to note that the low-linolenic lines Soyola and N98-4445 were derived from germplasm belonging to maturity group 4 to 5, while the other lines belong to maturity group 1 to 4. The mechanism for these mutations to cause the low-lin phenotype is unclear. One explanation was that there is another mutation located outside the coding region, probably in the promoter region, which caused the phenotype and is in linkage equilibrium with the markers detected within intron2. An analysis of the promoter sequence was therefore undertaken as described below.

It was important to note from Table 4 that mutant lines 6P248, T27111, T27190, T26767, T26830 and A5 failed to amplify with nearly all of the Fad3-1c locus-specific primers. This indicated that there was a large deletion at the Fad3-1c locus in these lines. The length of deletion varied slightly in different mutant lines. This result was consistent with an earlier study showing that A5 did indeed carry a deletion at Fad3-1c. Since a large portion of the entire gene was deleted, the enzyme catalyzing the conversion of linoleic acid to linolenic acid could be predicted to not function properly. As a result, plants carrying this mutant would produce less linolenic acid.

TABLE 4

Polymorphisms at the Fad3-1c locus
Sequence position

| Lines | 687 | 1129 | 1203 | 2316 | 3292 | 3360 | 3743 |
|---|---|---|---|---|---|---|---|
| 6P248 | NA | NA | NA | N/A | | | |
| T27111 | | NA | NA | NA | N/A | | |
| T27190 | | NA | NA | NA | N/A | | |
| T26767 | | NA | NA | NA | N/A | | |
| T26830 | | NA | NA | NA | N/A | | |
| A5 | NA | NA | NA | T | | | |
| C1640 | T(2) | * | A | | | | |
| Soyola | C(4) | T(2) | A | T | C(3) | A | A |
| N98-4445 | | C(2) | T | A | | | |
| A2247 | T | * | A | G | T(3) | * | * |
| AG1701 | | T | * | A | G | T(2) | * | * |
| AG1902 | | T | * | A | | T(2) | * | * |
| AG2402 | | T | * | A | G | T(2) | * | * |
| AG2703 | | T | * | A | | | | |
| AG3201 | | T | * | G | | | | |
| AG3302 | | T | * | A | | | | |
| AG3702 | | T | * | A | | | | |
| AJB2102J0C | | T | * | A | | | | |
| AJB2302K0C | | T | * | A | | | | |
| CSR2533 | | T | * | A | | | | |
| CSR2622N | | T | * | G | | | | |
| CSR3922N | | T | * | A | | | | |
| DKB19-51 | | T | * | A | | | | |
| DKB23-95 | | T | * | A | | | | |
| WP25920 | | T | * | A | | | | |

Note:
1. NA means no amplification detected
2. The number in the parenthesis indicates number of sequence reads in a given line Example 6

Isolation of the Promoter Region of Fad3-1c

To determine the factors that contribute to the low linolenic content in Soyola and N98-4445, efforts were made to clone the upstream region of the Fad3-1c gene. Three primers facing toward the upstream region were designed and the primers were used to amplify unknown promoter sequences according to the Genome Walking kit, purchased from CloneTech. An approximate 1 kb fragment was obtained from the A3244 line. The PCR product was directly sequenced after being treated with Exonuclease and Shrimp Alkaline Phosphatase. To identify polymorphisms associated with low-linolenic acid content, three new primer pairs were designed to cover the entire promoter and 5' end of the coding region, which were then used to amplify 24 different lines. Sequences from these amplicons were aligned to identify SNPs. Seven SNP were found in the promoter region (Table 5). Soyola carried a different allele at all seven positions from the other wild-type lines. These SNPs could be the determining factor for the low-linolenic phenotypes. To confirm the association, these SNPs will be tested on a population segregating for linolenic acid content.

TABLE 5

Polymorphisms at Fad3-1c Promoter Region
Position

| | 334 | 364 | 385 | 387 | 393 | 729 | 747 |
|---|---|---|---|---|---|---|---|
| Soyola | G | C | T | A | C | G | C |
| N98-4445 | G | C | T | A | C | G | C |
| Wildtypes (16 lines) | A | G | G | T | T | T | T |

Example 7

Low-Lin Marker Assay Validation

Taqman end point assays were designed from four SNPs identified above (Table 6). Assays were named after the SNP positions in the consensus sequences at a given locus. For example, FD3A842 meant SNP from Fad3-1a, at position 842 on the consensus sequence. A new marker name NS0193117 was later assigned to FD3A842 and used in production. The assays were validated on the same panel used in re-sequencing. FIG. 1A shows the allelogram of NS0193117. The allelic patterns from the Taqman assay were consistent with the sequences.

Figure 1B:
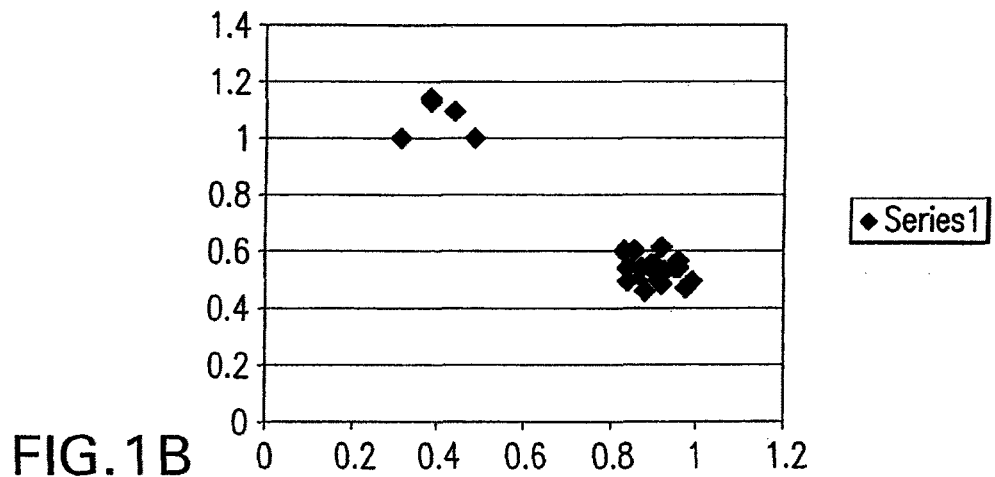
Figure 1C:
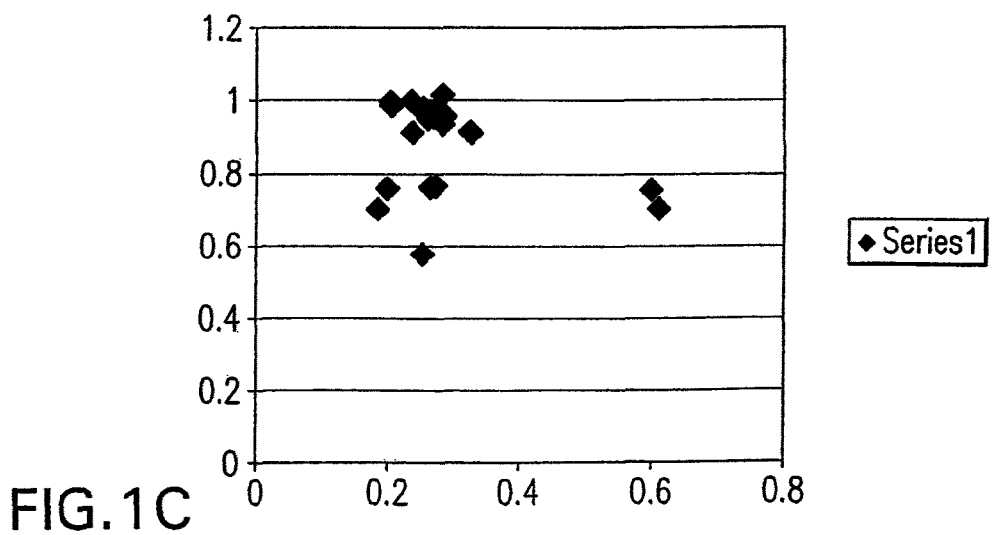

Two assays, FD3B2021A and FD3B2021B (NS0193115), were designed from Fad3-1b. FIG. 1B show the allelogram of NS0193115 on the sequencing panel. All four lines with low linolenic content had a different allele from the wild-type, corresponding well with the sequences. FIG. 1C shows the allelogram of NS0193116, derived from Fad3-1c position 687. Lines Soyola and N98-4445 showed a different allele from the others. All of the assay results corresponded to the sequence data.

The SNP markers were further tested on eight populations segregating for linolenic acid content (Table 7). Six SNPs that were known to be linked to the fanfan locus were also genotyped on the same populations. Since the populations were F4, they were treated as RI populations when used in the Mapmaker program. Heterozygous alleles were masked out.

NS0131053 is a marker located on linkage group B2/U26, where the fanfan locus resides. Table 7 shows that NS0193116 (Fad3-1c) is linked to NS0131053 by approximately 10 cM distance. Therefore, fad3c corresponds to fanfan, as we expected. Since NS0131053 was found to be linked to NS0193116 (fad3c), NS0131053 could also serve as a reference marker for low-linolenic line selection. Selection could be made based on both the null allele at NS0193116 and the low-linolenic allele at NS0131053. The data from these populations indicated that the Fad3-1a, -1b and -1c alleles were all independently inherited.

Figure 2:
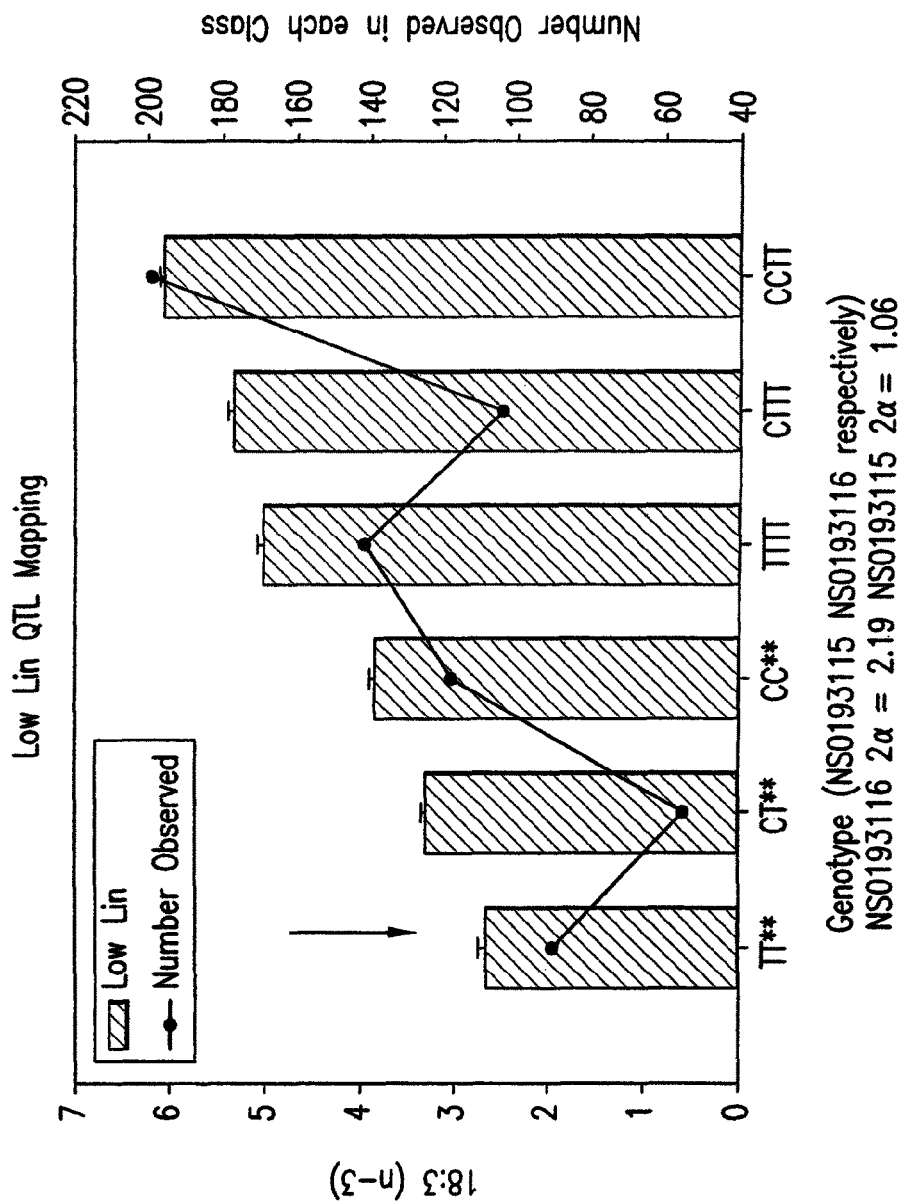
FIG. 2 shows the phenotypic values of Fad3-1b and Fad3-1c.

A combination of the NS0193115 and NS0193116 markers was found to provide accurate diagnosis for linolenic content. From the sequence results, it was clear that both Fad3-1b and -1c play a role in controlling the linolenic level in soybean. Mutant lines with the Fad3-1b (NS0193115) mutation alone contained about 4.2% linolenic acid while Fad3-1c (NS0193116) deletion alone contain about 3.4% (Table 8). Therefore, by combining selection for plants comprising markers for a double mutant at the Fad3-1b and Fad3-1c loci, even lower levels of linolenic acid could be obtained. FIG. 2 shows the phenotypic values of Fad3-1b and Fad3-1c. This clearly shows that the double mutants "TT**" have the lowest linolenic content while the double wild-types have the highest.

TABLE 6

Primers and Probes for Taqman Assays
(SEQ ID NOs:83-97, respectively)

| Locus | Primers and probes | Sequences |
|---|---|---|
| FAD3-A | FD3A842-842F | AGAAATCGCATCTGGAATGTGAAAGT |
| FAD3-A | FD3A842-842R | TGGGTTTCCTAGCACGCTATAAAAAT |
| FAD3-A | FD3A842-842V2 | CAACGACAGATGAAG |
| FAD3-A | FD3A842-842M2 | CAACGACAAATGAAG |
| FAD3-B | FD3B2021A-2021F | AGAAACTTACTCCATGTTACTCTGTCTATATGT |
| FAD3-B | FD3B2021A-2021R | TTGTGAAATAGAGAATTAATACCGCTTCGA |
| FAD3-B | FD3B2021A-2021V2 | AAAGGTGATGGATAACAT |
| FAD3-B | FD3B2021A-2021M2 | AAAAGGTAATGGATAACAT |
| FAD3-B | FD3B2021B-2021F | GGTGGTCTTACAACAGTAGATCGC |
| FAD3-B | FD3B2021B-2021R | CCGCTTCGATTAAATGATAATGTGGAAT |
| FAD3-B | FD3B2021B-2021V2 | AAAGGTGATGGATAACAT |
| FAD3-B | FD3B2021B-2021M2 | AAAAGGTAATGGATAACAT |
| FAD3-C | FD3C690A-690F | CCGGCTTTTTTGTTTGTCATTGGAA |
| FAD3-C | FD3C690A-690R | TCAAGATGTATTTCATTATTTTCTGAAACGCG |
| FAD3-C | FD3C690A-690V2 | CTATAAAAATTGAATCAATAGAAGAA |
| FAD3-C | FD3C690A-690M2 | AAAAATTGAATCAATAAAAGAA |

TABLE 7

Genetic linkage between NS0193116 and NS0131053

| | Map To Test: | |
|---|---|---|
| | Markers | Distance |
| Pop. 1 (1-96) | 1 N0131053 | 3.3 cM |
| | 5 N0193116 | 7.6 cM |
| | 2 N0129792 | 0.0 cM |
| | 3 N0096899 | — |
| | 11.0 cM 4 markers log-likelihood = −47.79 | |
| Pop 2 (97-192) 90 indiv | 1 N0131053 | 0.0 cM |
| | 3 N0193116 | — |
| | 0.0 cM 2 markers log-likelihood = −20.80 | |
| Pop. 4 (289-384) 66 indiv | 1 N0131053 | 4.4 cM |
| | 3 N0193116 | — |
| | 4.4 cM 2 markers log-likelihood = −21.10 | |

TABLE 7-continued

Genetic linkage between NS0193116 and NS0131053

| | Map To Test: | |
|---|---|---|
| | Markers | Distance |
| Pop. 6 (481-576) 94 indiv | 1 N0131053 | 6.7 cM |
| | 3 N0193116 | — |
| | 6.7 cM 2 markers log-likelihood = −35.24 | |
| Pop. 7 (577-672) 94 indiv | 1 N0131053 | 22.6 cM |
| | 3 N0193116 | — |
| | 22.6 cM 2 markers log-likelihood = −53.16 | |

TABLE 7-continued

Genetic linkage between NS0193116 and NS0131053

| | Map To Test: | |
|---|---|---|
| | Markers | Distance |
| Pop. 8 (673-768) 67 indiv | 1 N0131053 | 3.2 cM |
| | 2 N0099767 | 10.0 cM |
| | 4 N0193116 | — |
| | 13.2 cM 3 markers log-likelihood = −36.80 | |

TABLE 8

Percentage of Linolenic Content in Different Genotypes

| Q-NS0131053 | Total % | Q-NS0193116 | Total % | Q-NS0193115 | Total % |
|---|---|---|---|---|---|
| AA | 6.18 | | | CC | 5.26 |
| AT | 4.69 | TT | 5.53 | CT | 4.66 |
| TT | 3.76 | ** | 3.43 | TT | 4.17 |
| Grand Total | 4.75 | Grand Total | 4.75 | Grand Total | 4.75 |

REFERENCES

The following references, to the extent that they provide exemplary procedural or other details supplementary to those set forth herein, are specifically incorporated herein by reference.

U.S. Pat. No. 4,992,375
U.S. Pat. No. 5,015,580
U.S. Pat. No. 5,024,944
U.S. Pat. No. 5,416,011
U.S. Pat. No. 5,545,545
U.S. Pat. No. 5,637,785
U.S. Pat. No. 6,031,154
U.S. Pat. No. 6,140,085
U.S. Pat. No. 6,184,440
U.S. Pat. No. 6,184,442
U.S. Pat. No. 6,369,302
U.S. Pat. No. 6,486,383
U.S. Pat. No. 6,774,284
Allard, In: *Principles of Plant Breeding*, John Wiley & Sons, NY, 50-98, 1960.
Beachy et al., *Ann. rev. Phytopathol.* 28:451 (1990
Boerma and Moradshahi, *Crop Sci.,* 15:858-861, 1975.
Borthwick and Parker, *Bot. Gaz.,* 100:374-387, 1938.
Brim and Stuber, *Crop Sci.,* 13:528-530, 1973.
Byrum, et al., *Theor. Appl. Genet.,* 94:356-359, 1997.
Charest et al., *Plant Cell Rep.* 8:643 (1990
Christianson et al., *Science,* 222:632-634, 1983.
Comai et al., *Nature* 317:741-744 (1985)
Criswell and Hume, *Crop Sci.,* 12:657-660, 1972.
Dhir et al., *Plant Cell Rep.,* 10(2):97-101, 1991.
Dutton and Sommer, *Biotechniques,* 11(6):700-7002., 1991.
Dutton et al., *J. Am. Oil Chem. Soc.,* 28:115-118, 1951.
Eichholtz et al., *Somatic Cell Mol. Genet.* 13:67 (1987)
Elliot et al., *Plant Molec. Biol.* 21:515 (1993
European Appln. 0 242 246
Fehr et al., *Crop Sci.,* 32:903-906, 1992.
Fehr, In: *Theory and Technique,* and *Crop Species Soybean,* Iowa State Univ., Macmillian Pub. Co., NY, (1)(2):360-376, 1987b.
Fehr, In: Soybeans: Improvement, Production and Uses, 2nd Edition, Manograph., 16:249, 1987a.
Fehr, In: *Hybridization of Crop Plants,* Fehr and Hadley (Eds.), Am. Soc. Agron. and Crop Sci. Soc. Am., Madison, Wis., 90-599, 1980.
Finer et al., In: *Soybean: Genetics, Molecular Biology and Biotechnology,* CAB Intl., Verma and Shoemaker (ed), Wallingford, Oxon, UK, 250-251, 1996.
Fraley et al., *Proc. Natl. Acad. Sci. USA,* 80:4803, 1983.
Geiser et al., *Gene,* 48:109, 1986.
Gordon-Kamm et al., *Plant Cell,* 2:603-618, 1990.
Hamner, In: *The Induction of Flowering: Some Case Histories,* Evans (ed), Cornell Univ. Press, Ithaca, N.Y., 62-89, 1969.
Hartweck et al., *In Vitro Cell. Develop. Bio.,* 24:821-828, 1988.
Hu et al., *N. Engl. J. Med.,* 337:1491-1499, 1997.
Johnson and Bernard, In: *The Soybean,* Norman (ed), Academic Press, NY, 1-73, 1963.
Jones et al., *Science,* 266:789, 1994.
Knutzon et al., *Proc. Natl. Acad. Sci. USA,* 89:2624, 1992.
Lander and Botstein, *Genetics,* 121(1):185-199, 1989.
Lee et al., *EMBO J.,* 7:1241, 1988.
Logemann et al., *Bio/Technology,* 10:305, 1992.
Lui and White, *J. Am. Oil Chem. Soc.,* 69:528-532, 1992.
Marshall et al., *Theor. Appl. Genet.,* 83:435, 1992.
Martin et al., *Science,* 262:1432, 1993.
Miki et al., *Theor. Appl. Genet.,* 80:449, 1990.
Mindrinos et al., *Cell,* 78:1089, 1994.
Myers, EPO 0273085
Orita et al., *Genomics,* 8(2):271-278, 1990.
PCT Appln. US93/06487
PCT Appln. WO93/19181
PCT Appln. WO96/30517
Pen et al., *Bio/Technology,* 10:292, 1992.
Poehlman and Sleper, In: *Breeding Field Crops,* Iowa State University Press, Ames, 1995.
Przibila et al., *Plant Cell,* 3:169, 1991.
Rahman and Takagi, *Theor. Appl. Genet.,* 94:299-302, 1997.
Rahman et al., *Crop Sci.,* 38:702-706, 1998.
Reiter et al., *Proc. Natl. Acad. Sci. USA,* 89(4):1477-1481, 1992.
Ross et al., *Crop Sci.,* 40:383-386, 2000.
Shah et al., *Science,* 233:478, 1986.
Shanmugasundaram and Tsou, *Crop Sci.,* 18:598-601, 1978.
Shibles et al., In: *Crop Physiology, Some Case Histories,* Evans (ed), Cambridge Univ. Press, Cambridge, England, 51-189, 1975.
Shiroza et al., *J. Bacteol.,* 170:810, 1988.
Simmonds, In: *Principles of crop improvement,* Longman, Inc., NY, 369-399, 1979.
Sneep and Hendriksen, In: *Plant breeding perspectives,* Wageningen (ed), Center for Agricultural Publishing and Documentation, 1979.
Sommer et al., *Biotechniques,* 12(1):82-87, 1992.
Stalker et al., *Science,* 242:419-423, 1988.
Steinmetz et al., *Mol. Gen. Genet.,* 20:220, 1985.
Stoisin et al., *Crop Sci.,* 38:1441-1444, 1998.
Vanden Elzen et al., *Plant Mol. Biol.,* 5:299, 1985.
Wright et al., *Plant Cell Reports,* 5:150-154, 1986.

The invention claimed is:

1. A plant of an agronomically elite soybean variety having a commercially significant yield and a mid/low-linolenic acid content, comprising a Fad3-1b allele and a Fad3-1c allele each of which confer decreased linolenic acid content, and wherein the Fad3-1c allele comprises: (i) a single nucleotide polymorphism at a position in the Fad3-1c gene sequence corresponding to nucleotide 687, 1129, 1203, 2316, 3292, 3360 or 3743 of SEQ ID NO:2; or (ii) a single nucleotide polymorphism at a position in the Fad3-1c promoter corresponding to nucleotide 334, 364, 385, 387, 393, 729 or 747 of SEQ ID NO:3.

2. The plant of claim 1, wherein the linolenic acid content is further defined as selected from the group consisting of from about 1.2% to about 3.0% by weight of total seed fatty acids, from about 1.5% to about 3.0% by weight of total seed fatty acids, from about 2% to about 2.6% by weight of total seed fatty acids, from about 2% to about 3% by weight of total seed fatty acids, from about 1% to about 2.6% by weight of total seed fatty acids, from about 1% to about 2.2% by weight of total seed fatty acids, from about 1.6% to about 2.6% by weight of total seed fatty acids, and from about 2% to about 2.4% by weight of total seed fatty acids.

3. A plant part of the plant of claim 1.

4. The plant part of claim 3, further defined as pollen, an ovule, a meristem or a cell.

5. A seed of the plant of claim 1.

6. A tissue culture of regenerable cells of the plant of claim 1, wherein the tissue culture regenerates soybean plants expressing the physiological and morphological characteristics of the plant of claim 1.

7. The tissue culture of claim 6, wherein the regenerable cells are embryos, meristematic cells, pollen, leaves, roots, root tips or flowers.

8. A soybean plant regenerated from the tissue culture of claim 6, wherein the regenerated soybean plant expresses the physiological and morphological characteristics of the plant of claim 1.

9. The plant of claim 1, further defined as comprising a transgene.

10. The plant of claim 9, wherein the transgene is further defined as conferring a trait selected from the group consisting of herbicide tolerance; disease resistance;
   insect or pest resistance; altered fatty acid, protein or carbohydrate metabolism; increased grain yield; altered plant maturity, and altered morphological characteristics.

11. The plant of claim 9, wherein the transgene confers tolerance to glyphosate herbicide.

12. The plant of claim 1, defined as prepared by a method comprising the steps of:
   a) crossing first and second soybean plants, wherein the first and second plants collectively comprise a Fad3-1b allele and a Fad3-1c allele each of which confer decreased linolenic acid content, wherein the first plant comprises at least one of the Fad3-1b or Fad3-1c alleles, and wherein the second plant comprises a commercially significant yield;
   b) assaying progeny soybean plants resulting from the crossing for yield and for the presence of polymorphisms located in a soybean plant genomic region within 50 cM of said Fad3-1b and Fad3-1c alleles; and
   c) selecting at least a first progeny plant comprising said polymorphisms and a commercially significant yield to obtain the plant of claim 1;
   wherein the Fad3-1c allele comprises: (i) a single nucleotide polymorphism at a position in the Fad3-1c gene sequence corresponding to nucleotide 687, 1129, 1203, 2316, 3292, 3360 or 3743 of SEQ ID NO:2; or (ii) a single nucleotide polymorphism at a position in the Fad3-1c promoter corresponding to nucleotide 334, 364, 385, 387, 393, 729 or 747 of SEQ ID NO:3.

13. The plant of claim 1, wherein the plant comprises at least a first polymorphism in a soybean plant genomic region within 50 cM of a Fad3-1b or Fad3-1c allele conferring decreased linolenic acid content.

14. The plant of claim 13, comprising polymorphisms in a soybean plant genomic region within 50 cM of both of said Fad3-1b and Fad3-1c alleles.

15. The plant of claim 13, wherein the first polymorphism comprises a single nucleotide polymorphism at a position in the Fad3-1b gene sequence corresponding to nucleotide 2021 of SEQ ID NO:1.

16. The plant of claim 13, wherein the first polymorphism comprises a single nucleotide polymorphism at a position in the Fad3-1c gene sequence corresponding to nucleotide 687, 1129, 1203, 2316, 3292, 3360 or 3743 of SEQ ID NO:2.

17. The plant of claim 13, wherein the first polymorphism comprises a deletion in the Fad3-1c gene sequence.

18. The plant of claim 13, wherein the first polymorphism comprises a single nucleotide polymorphism at a position in the Fad3-1c promoter corresponding to nucleotide 334, 364, 385, 387, 393, 729 or 747 of SEQ ID NO:3.

19. The plant of claim 12, wherein the Fad3-1b allele comprises a single nucleotide polymorphism at a position in the Fad3-1b gene sequence corresponding to nucleotide 2021 of SEQ ID NO:1.

* * * * *